United States Patent
Brockman et al.

(10) Patent No.: US 8,147,451 B2
(45) Date of Patent: Apr. 3, 2012

(54) REPROGRAMMABLE FLUID DELIVERY SYSTEM AND METHOD OF USE

(75) Inventors: Christopher S. Brockman, Kalamazoo, MI (US); Mark A. Wasserman, Delton, MI (US); David E. Hershberger, Kalamazoo, MI (US); Jacob C. Foor, Mattawan, MI (US); Michael Strickler, Richland, MI (US); Jason D. Toman, Swissvale, PA (US)

(73) Assignee: Stryker Corporation, Kalamazoo, MI (US)

( * ) Notice: Subject to any disclaimer, the term of this patent is extended or adjusted under 35 U.S.C. 154(b) by 1566 days.

(21) Appl. No.: 11/351,913

(22) Filed: Feb. 10, 2006

(65) Prior Publication Data

US 2006/0184121 A1 Aug. 17, 2006

Related U.S. Application Data

(60) Provisional application No. 60/652,454, filed on Feb. 11, 2005.

(51) Int. Cl.
*A61M 1/00* (2006.01)
(52) U.S. Cl. .......................................... 604/151; 604/65
(58) Field of Classification Search .............. 604/73–76, 604/118–157, 65–67
See application file for complete search history.

(56) References Cited

U.S. PATENT DOCUMENTS

| | | | |
|---|---|---|---|
| 4,384,578 A * | 5/1983 | Winkler | 604/114 |
| 4,627,840 A | 12/1986 | Cuadra et al. | |
| 4,650,469 A * | 3/1987 | Berg et al. | 604/131 |
| 5,743,878 A * | 4/1998 | Ross et al. | 604/131 |
| 5,764,539 A | 6/1998 | Rani | |
| 5,807,075 A | 9/1998 | Jacobsen et al. | |
| 5,960,085 A | 9/1999 | de la Huerga | |
| 6,589,229 B1 | 7/2003 | Connelly et al. | |

(Continued)

FOREIGN PATENT DOCUMENTS

DE 3827444 A1 2/1990

(Continued)

OTHER PUBLICATIONS

English language Abstract for German Patent Application No. DE38 27 444 A1, published Feb. 15, 1990.

(Continued)

*Primary Examiner* — Kevin C Sirmons
*Assistant Examiner* — Phillip Gray
(74) *Attorney, Agent, or Firm* — Howard & Howard Attorneys PLLC

(57) ABSTRACT

A fluid delivery system is provided for delivering fluid to a patient. The system comprises a reservoir for storing the fluid to be delivered to the patient and a fluid discharge device operatively coupled to the reservoir for delivering the fluid from the reservoir to the patient. A controller is configured to operate the fluid discharge device. An input device is in electronic communication with the controller and configured for setting at least one operating parameter of the system. The controller operates the fluid discharge device based on the at least one operating parameter and locks the system after the at least one operating parameter is set such that the at least one operating parameter is unable to be modified. A display is in electronic communication with the controller to at least periodically display a code for resetting the at least one operating parameter. The code is altered at least once during use. The controller is further configured to unlock the system upon receiving the code thereby allowing a user to reset the at least one operating parameter.

12 Claims, 29 Drawing Sheets

U.S. PATENT DOCUMENTS

| | | |
|---|---|---|
| 6,740,075 B2 | 5/2004 | Lebel et al. |
| 6,852,104 B2 | 2/2005 | Blomquist |
| 2002/0116509 A1 | 8/2002 | DeLaHuerga |
| 2002/0120236 A1 | 8/2002 | Diaz |
| 2003/0065370 A1 | 4/2003 | Lebel et al. |
| 2004/0225252 A1 | 11/2004 | Gillespie, Jr. et al. |

FOREIGN PATENT DOCUMENTS

| | | |
|---|---|---|
| EP | 0405148 A1 | 5/1990 |
| WO | 8605993 | 10/1986 |

OTHER PUBLICATIONS

English language Abstract for European Patent Application No. EP 0 405 148 A1, published Jan. 2, 1991.

PCT International Search Report and Written Opinion, International Application No. PCT/US2006/004904; International Filing Date Feb. 10, 2006.

* cited by examiner

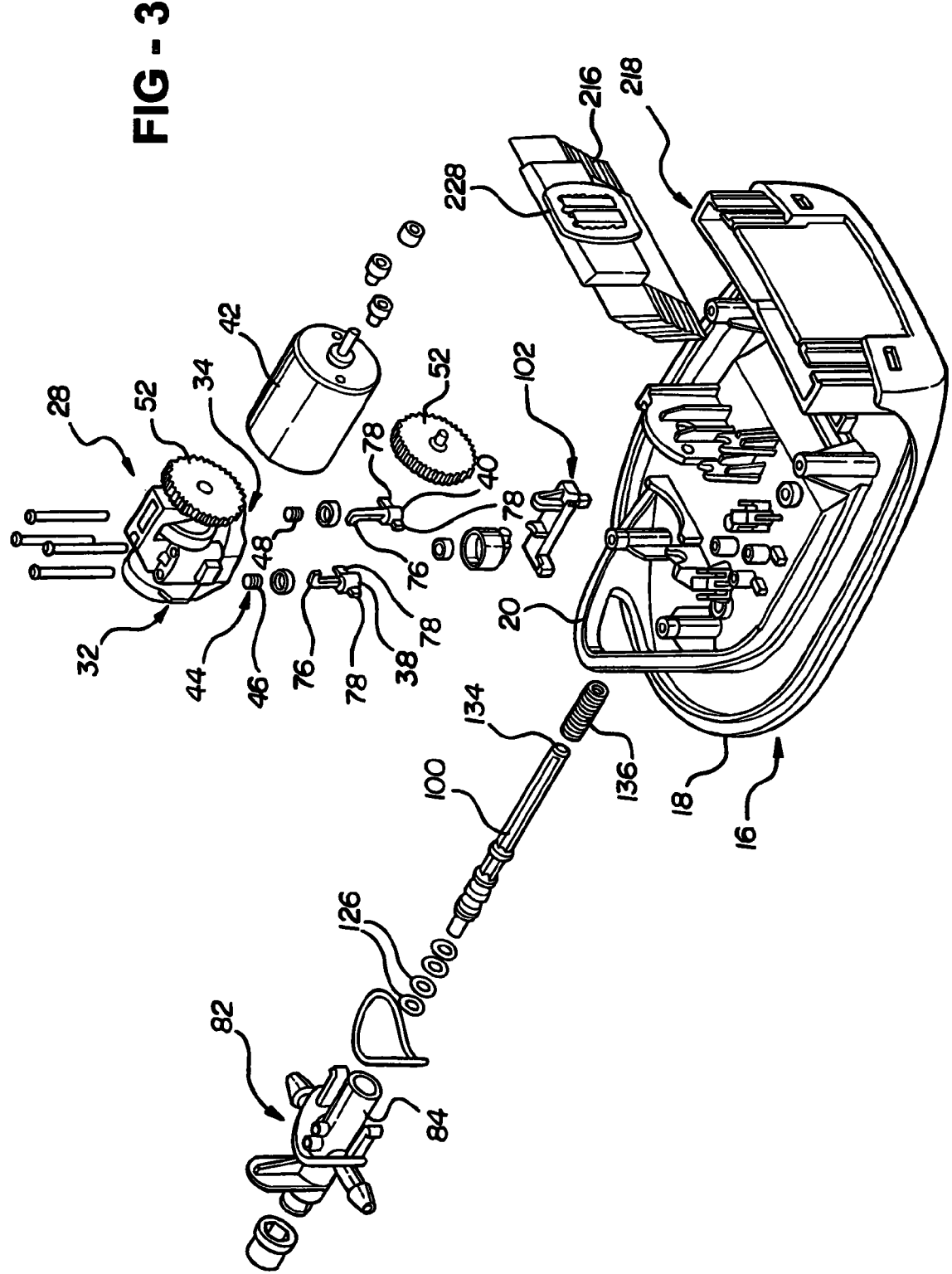

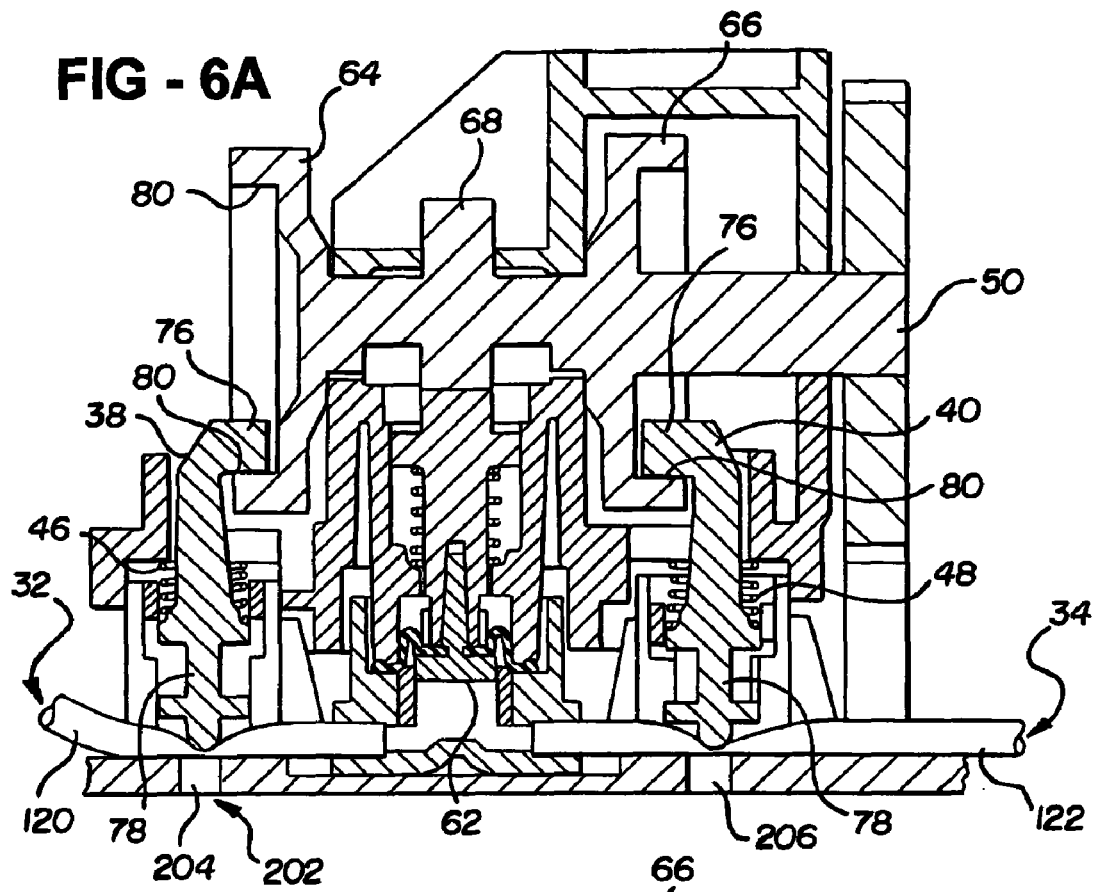
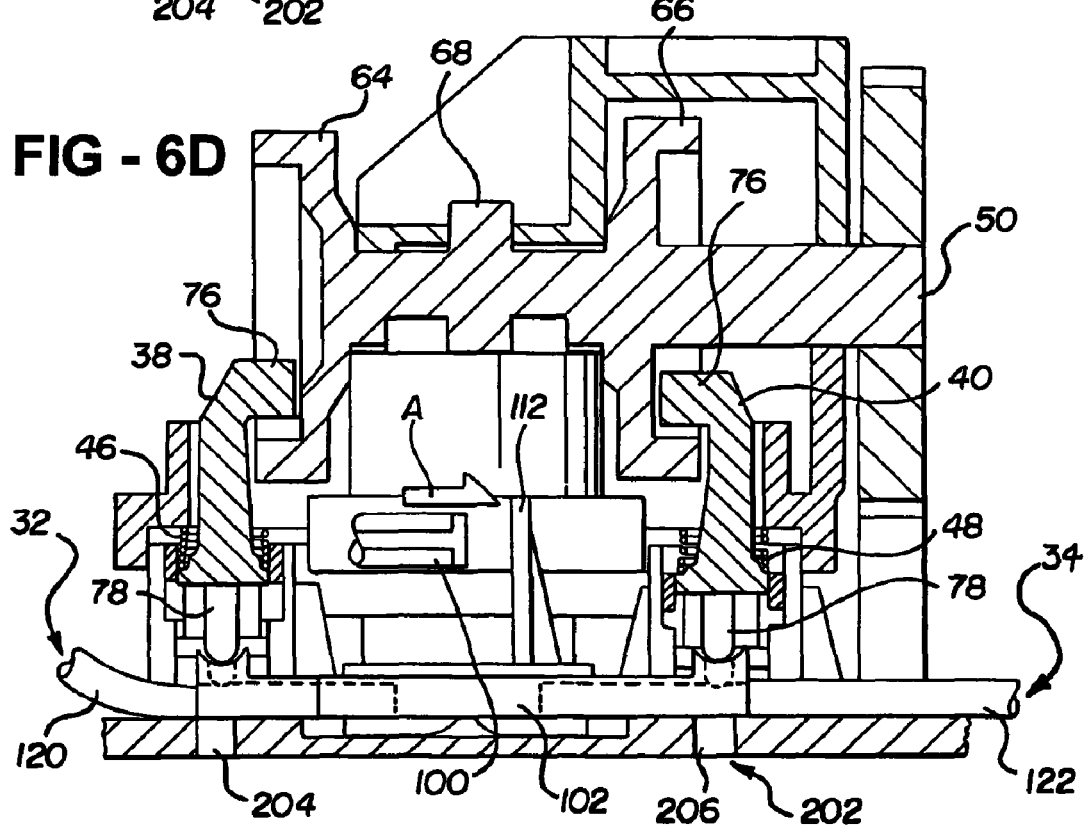

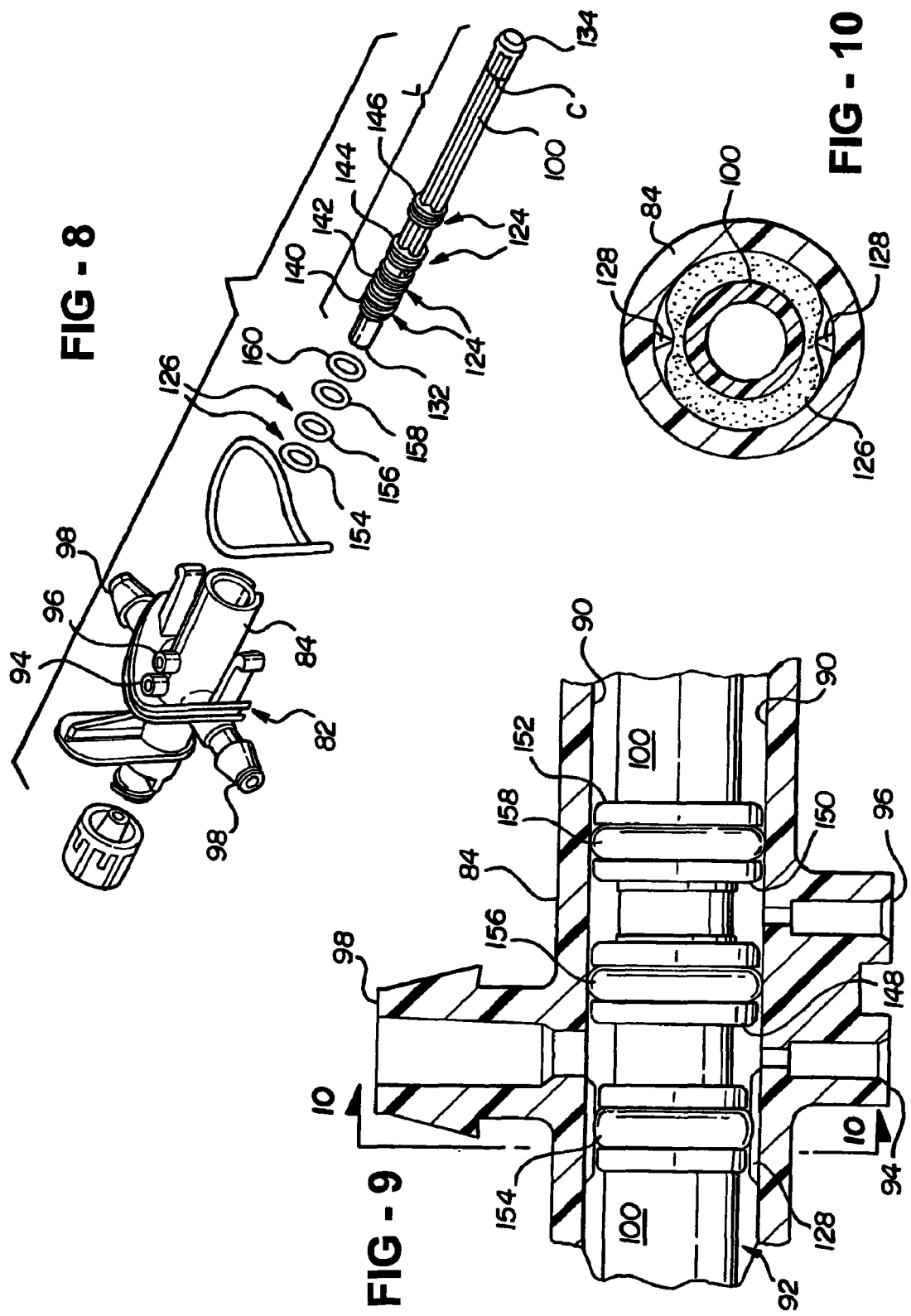

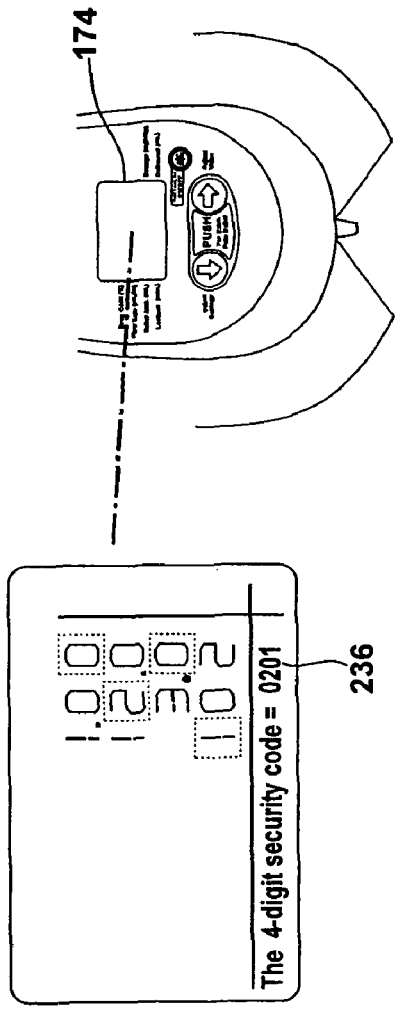
FIG - 26
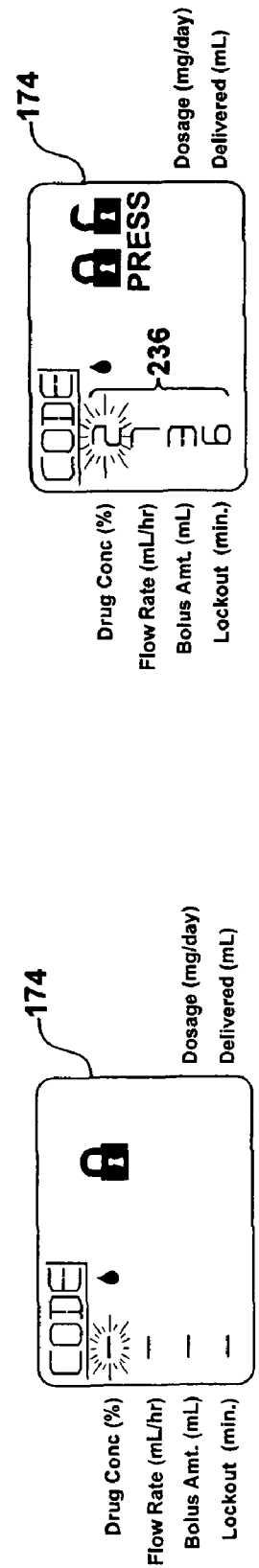
FIG - 27B
FIG - 27A

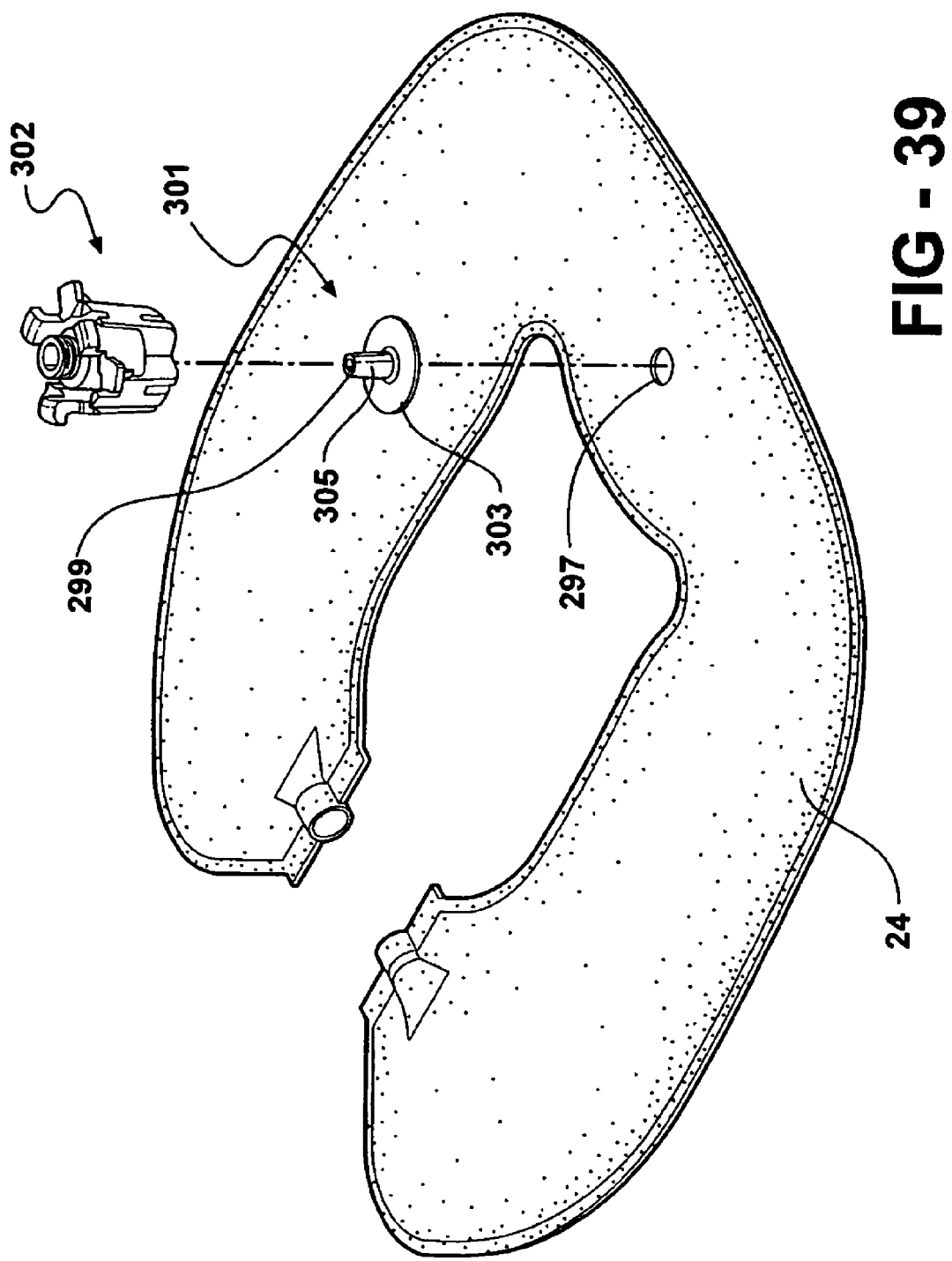

REPROGRAMMABLE FLUID DELIVERY SYSTEM AND METHOD OF USE

CROSS-REFERENCE TO RELATED APPLICATIONS

This application claims the benefit of U.S. provisional patent application Ser. No. 60/652,454, filed on Feb. 11, 2005, the advantages and disclosure of which are hereby incorporated by reference.

FIELD OF THE INVENTION

The present invention relates generally to a fluid delivery system for delivering fluid such as medication to a patient. The fluid delivery system is primarily used throughout the medical profession to deliver pain control medication and other medications subcutaneously or percutaneously to the patient after a surgical, or some other medical, procedure. More specifically, the present invention relates to the fluid delivery system being reprogrammed using a security code.

BACKGROUND OF THE INVENTION

Fluid delivery systems for medical use are well known in the art. Typically, these systems are used to deliver pain control medication and other medications such as insulin to a patient. A typical system includes a reservoir for storing the fluid to be delivered to the patient and a pump assembly in operative communication with the reservoir for delivering the fluid from the reservoir to the patient. Often, a controller is programmed to operate the pump assembly based on a plurality of operating parameters such as flow rate, bolus amount, and the like. An input device in electronic communication with the controller is used to set values for the plurality of operating parameters. Once set, the controller operates the pump assembly based on the operating parameters. In many prior art systems, once the values of the operating parameters are established, the system is locked to prevent further access to reset the values of the operating parameters. In some cases, however, it may be desirable to reset the operating parameters such as when the patient requires additional medication.

For instance, in U.S. Pat. No. 6,740,075 to Lebel et al., an implantable infusion pump is disclosed that has certain operating parameters that may be reset based on changing conditions. One such operating parameter is a diagnostic medication delivery rate. In Lebel et al., the pump communicates with an external device that requires a password in order to change the diagnostic medication delivery rate. The password may be established by a medical professional using the external device, or may be a factory password derived from the system. The factory password may be fixed or variable. If variable, the password may be based on a variable parameter such as the date and/or time reflected on the external device. However, Lebel et al. does not disclose a system that takes care to ensure that the user, e.g., the medical professional, will not forget the password.

Therefore, there is a need in the art for a fluid delivery system that is capable of being reprogrammed to reset values for a plurality of operating parameters using a security code that is easily remembered by the user.

BRIEF SUMMARY OF THE INVENTION AND ADVANTAGES

The present invention provides a fluid delivery system for delivering fluid to a patient. The system comprises a reservoir for storing the fluid to be delivered to the patient and a fluid discharge device operatively coupled to the reservoir for delivering the fluid from the reservoir to the patient. A controller is configured for operating the fluid discharge device. An input device is in electronic communication with the controller and configured for setting at least one operating parameter of the system. The controller operates the fluid discharge device based on the at least one operating parameter and locks the system after the at least one operating parameter is set such that the at least one operating parameter is unable to be modified. In some cases, however, it is desirable to reset the at least one operating parameter. A display is electronically coupled to the controller to at least periodically display a code for resetting the at least one operating parameter. The code is altered by the controller at least once during use of the system such that the code is variable. The controller is further configured to unlock the system upon receiving the code thereby allowing a user to reset the at least one operating parameter.

In another embodiment, the code is continuously displayed on the display and altered at predetermined time intervals.

In yet another embodiment of the present invention, the code is associated with values set for a plurality of operating parameters and displayed on the display in a predetermined pattern.

A method of delivering fluid to the patient from the system is also provided. The method comprises the steps of setting the at least one operating parameter of the system and locking the system after setting the at least one operating parameter such that the at least one operating parameter is unable to be modified. Fluid is delivered to the patient based on the setting of the at least one operating parameter and while the system is locked. The code is at least periodically displayed and altered at least once during use. The system is unlocked upon receiving the code thereby allowing the user to reset the at least one operating parameter.

By using the code that is at least periodically displayed on the display and altered at least once during use, the user can more easily remember the code to reset the at least one operating parameter. As a result, instead of users, such as medical professionals, being required to remember different codes for different patients, or instead of using the same code for all systems, the present invention provides a security code that is easily recognized by the user. The present invention allows for reprogramming the system, while maintaining a certain aspect of security by altering the code at least once during use.

BRIEF DESCRIPTION OF THE SEVERAL VIEWS OF THE DRAWINGS

Advantages of the present invention will be readily appreciated as the same becomes better understood by reference to the following detailed description when considered in connection with the accompanying drawings wherein:

FIG. 3 is an exploded perspective view of the system illustrating a port, a plunger, the pump assembly including a motor and first and second pinch levers, an actuator, and the base including an integral storage cavity for the carrying strap;

FIG. 6A is a partially cross-sectional side view of a camshaft, the pump assembly, and the first and second pinch levers illustrating the pinch levers in a closed position to pinch medication inlet and outlet tubes;

FIG. 6D is a partially cross-sectional side view of the system, as disclosed in FIG. 6A, in combination with the plunger and the actuator, with the actuator retaining the pinch levers in the open position;

FIG. 8 is an exploded perspective view of the port and the plunger;

FIG. 9 is an enlarged partially cross-sectional top view of the plunger disposed in the port illustrating a first, second, and third fluid connector;

FIG. 10 is a partially cross-sectional side view taken along line 10-10 in FIG. 9 illustrating a seal disposed about the plunger being depressed by leak ribs extending from the port;

FIGS. 25A-25F illustrate various views of the display of the system for setting a plurality of operating parameters;

FIG. 26 illustrates a scheme for displaying a code on the display of the system;

FIGS. 27A-27B illustrate various views of the display for unlocking the system after the plurality of operating parameters have been set;

FIG. 39 is a perspective assembly view of the valve, a flanged connector for the valve, and the reservoir of the system

DETAILED DESCRIPTION OF THE INVENTION

Figure 19:
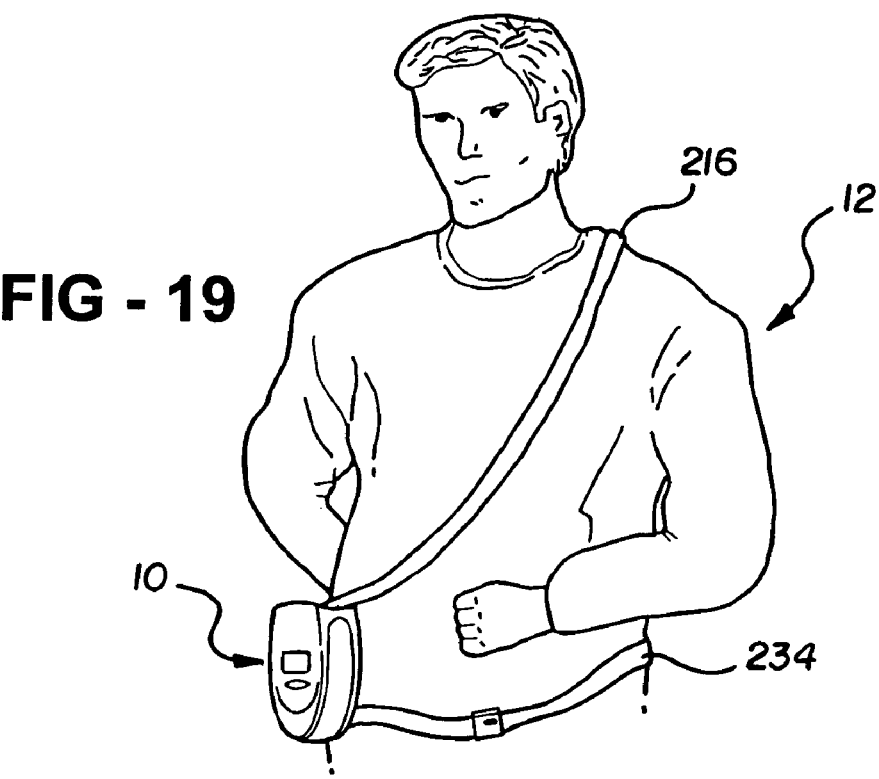
FIG. 19 is a perspective view of the patient using the carrying strap as a shoulder strap to carry the system.

Referring to the Figures, wherein like numerals indicate like or corresponding parts throughout the several views, a fluid delivery system is generally disclosed at 10. The fluid delivery system 10, hereinafter described as the system 10, delivers fluid such as medication to a patient 12 (refer to FIG. 19). Other fluids such as saline, nutrient-enriched fluids, and the like could also be delivered to the patient using the system 10. For purposes of illustration, the system 10 shall be described as being used to deliver pain control medication and other medications to the patient 12 after a surgical, or some other medical, procedure. As disclosed in FIG. 1A, the system 10 is used in combination with an infusion tube set 14 to deliver the medication to the patient 12. Typically, the infusion tube set 14 would attach to a catheter (not shown) inserted into the patient at an infusion site to deliver medication from the system 10 to the infusion site.

The system 10 of the present invention is suitable for complete sterilization by a sterilization fluid including, but not limited to, ethylene oxide (EtO) gas. Additionally, certain liquids may be used to sterilize the system 10. For descriptive purposes only, the terminology of "medication" and or "sterilization" fluid may also be described throughout simply as fluid.

Figure 2:
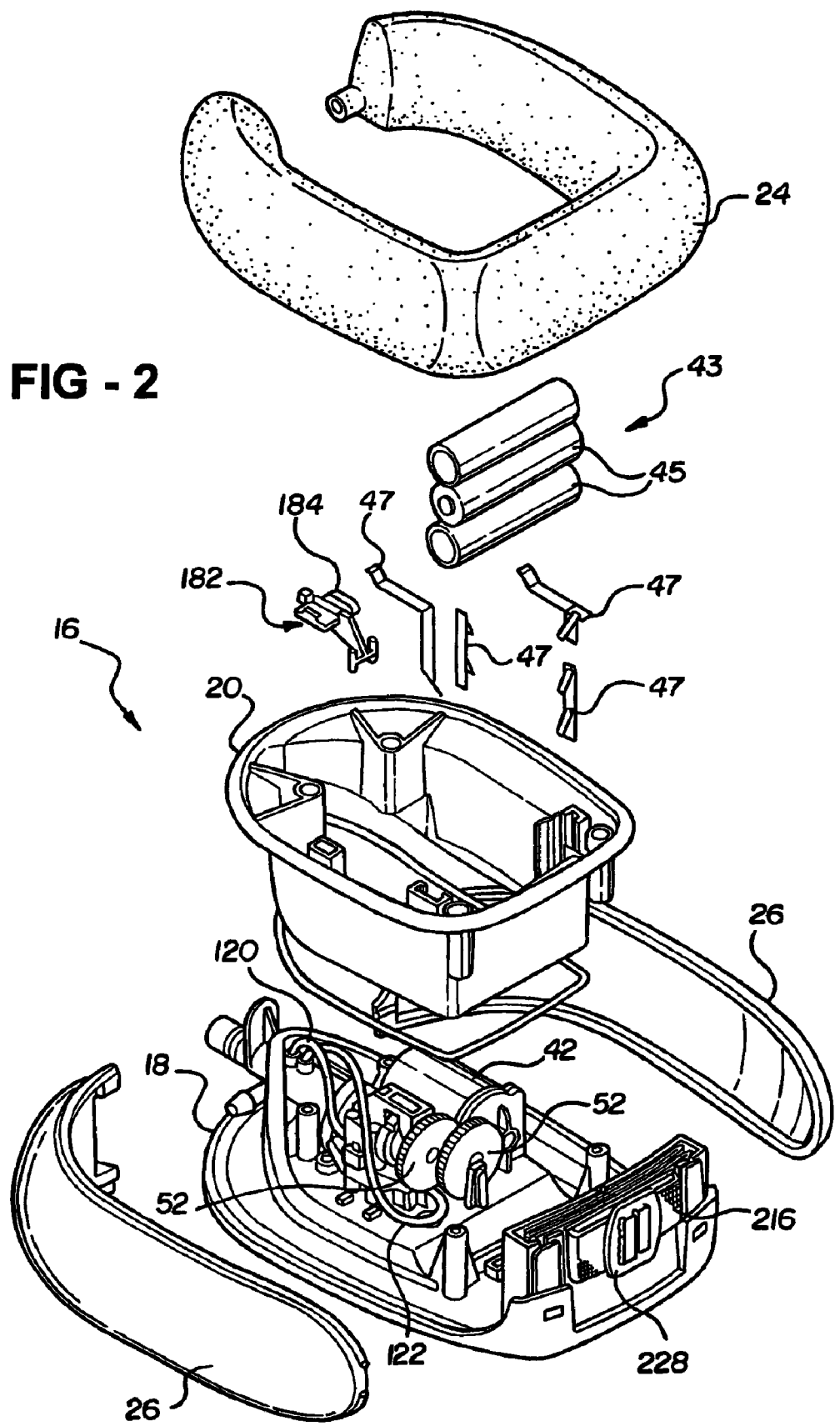
FIG. 2 is an exploded perspective view of the system illustrating a reservoir, a base, reservoir casings, a pump assembly, and a carrying strap of the system.
Figure 4:
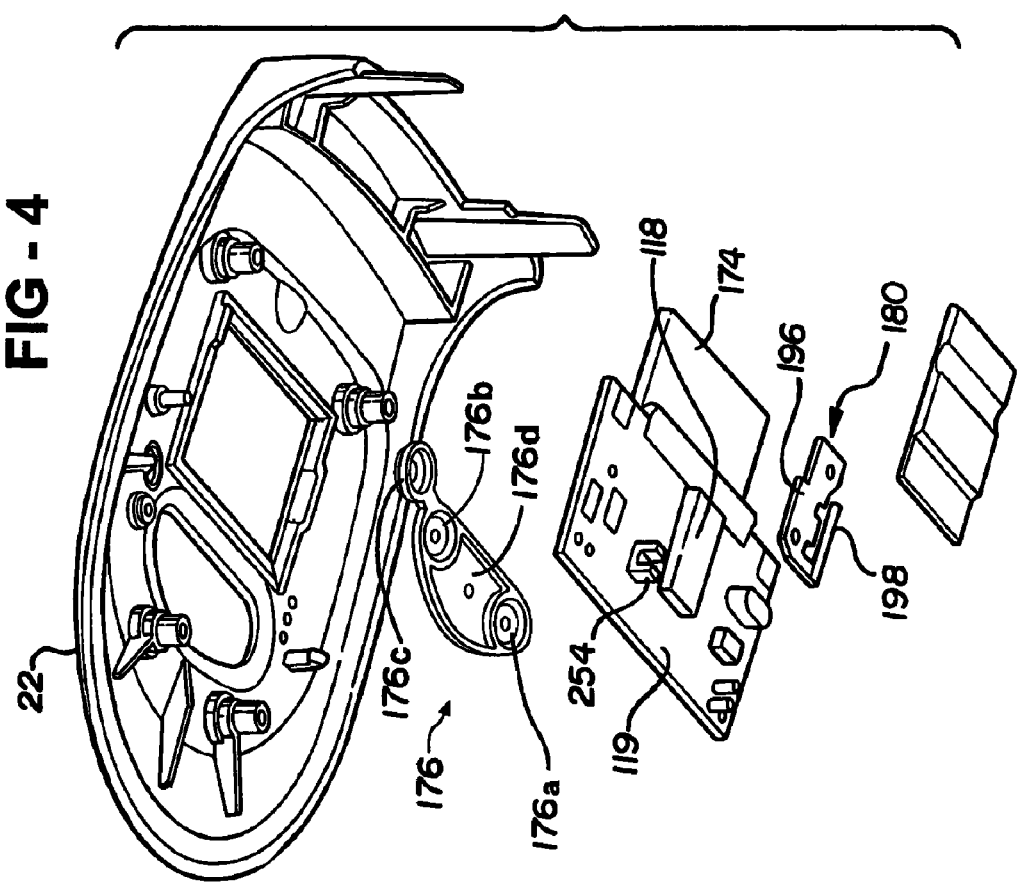
FIG. 4 is an exploded perspective view of the system illustrating an underside of a cover, an input device, an electronic controller and display, and a detection film having a cantilever portion.

Referring primarily to FIGS. 2-4, the system 10 includes a housing 16. The housing 16 comprises a base 18, a middle housing 20 mounted to the base 18 and a cover 22. The base 18, middle housing 20, and cover 22 are preferably mounted together via screws 23. The system 10 also includes a reservoir 24 supported by the base 18 and disposed about the middle housing 20. The reservoir 24 stores the supply of medication that is to be delivered to the patient 12. Preferably, the reservoir 24 is formed of a flexible, yet durable, plastic material. The system 10 further includes a reservoir casing 26 disposed between the base 18 and the cover 22. The reservoir casing 26 at least partially surrounds the reservoir 24 to protect the medication that is to be delivered to the patient 12. The preferred embodiment of the present invention includes two reservoir casings 26 that surround the reservoir 24 to protect the medication. Of course, it is to be understood that the reservoir casing 26 may be a unitary component and still adequately surround the reservoir 24 to protect the medication. The system 10 is portable and the reservoir casings 26 are particularly useful when the patient 12 is carrying the system 10

Referring primarily to FIGS. 2, 3, and 5-6D, a pump assembly 28 is supported by the base 18. Specifically, the pump assembly 28 is mounted to the base 18. As understood by those skilled in the art, the pump assembly 28 is responsible for delivering the medication to the patient 12. More specifically, the pump assembly 28 is operatively coupled to the reservoir 24 to deliver the medication from the reservoir 24 to the patient 12. As described below, the pump assembly 28 also serves to prevent inadvertent delivery of the medication to the patient 12. The description of the pump assembly 28 below is only one embodiment of a fluid discharge device that could be used with the system 10. Other fluid discharge devices could also be used with the system 10 to deliver the medication to the patient 12. The pump assembly 28 is also described in U.S. Pat. No. 6,679,862 to Diaz et al., hereby incorporated by reference.

Figure 5:
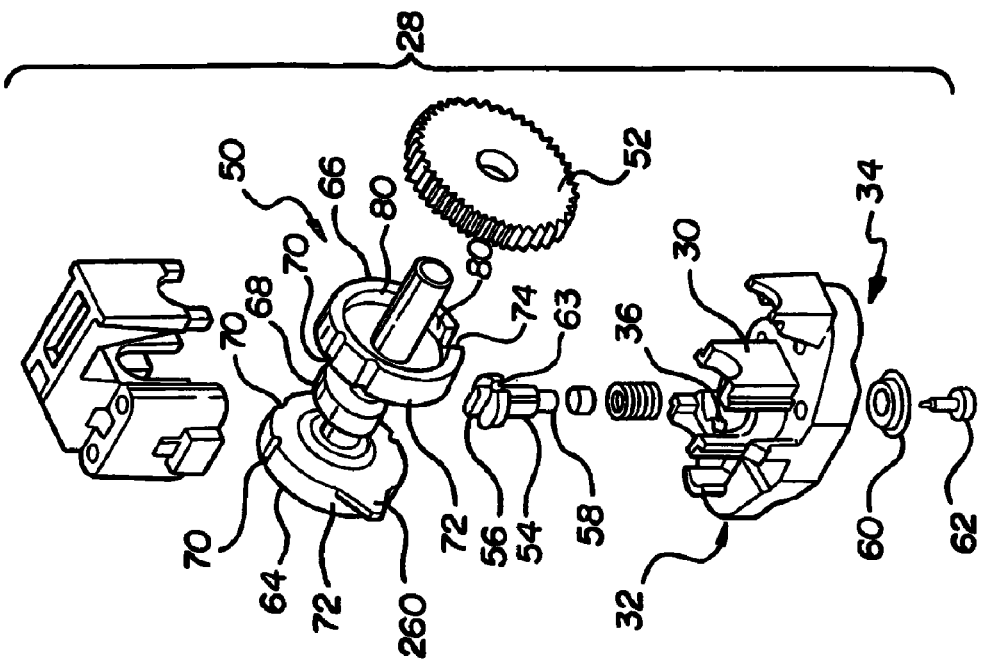
FIG. 5 is an exploded perspective view of the pump assembly.

As disclosed best in FIG. 5, the pump assembly 28 includes a pump housing 30 having a pump inlet 32 and a pump outlet 34. The pump housing 30 also has at least one detent 36. The at least one detent 36 is described below. The pump inlet 32 and the pump outlet 34 alternate between an open and a closed state to deliver the medication to the patient 12. Referring now to FIGS. 3, and 6A-6D, a first pinch lever 38, also referred to as a pinch valve, is disposed at the pump inlet 32 and a second pinch lever 40 or valve is disposed at the pump outlet 34. The first pinch lever 38 functions to alternate the pump inlet 32 between the open and the closed state, and the second pinch lever 40 functions to alternate the pump outlet 34 between the open and the closed state.

Figure 6B:
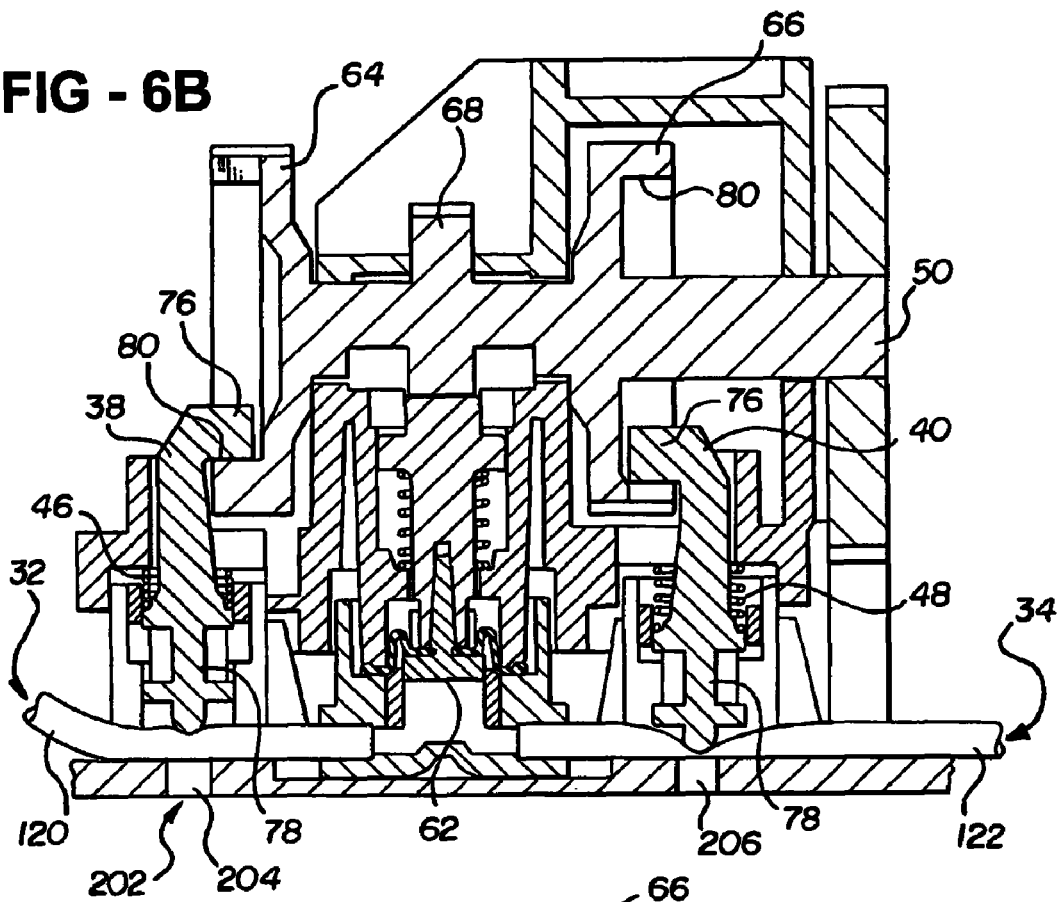
FIG. 6B is a partially cross-sectional side view of the system, as disclosed in FIG. 6A, illustrating the first pinch lever in an open position and the second pinch lever in a closed position to draw medication into the pump assembly.
Figure 6C:
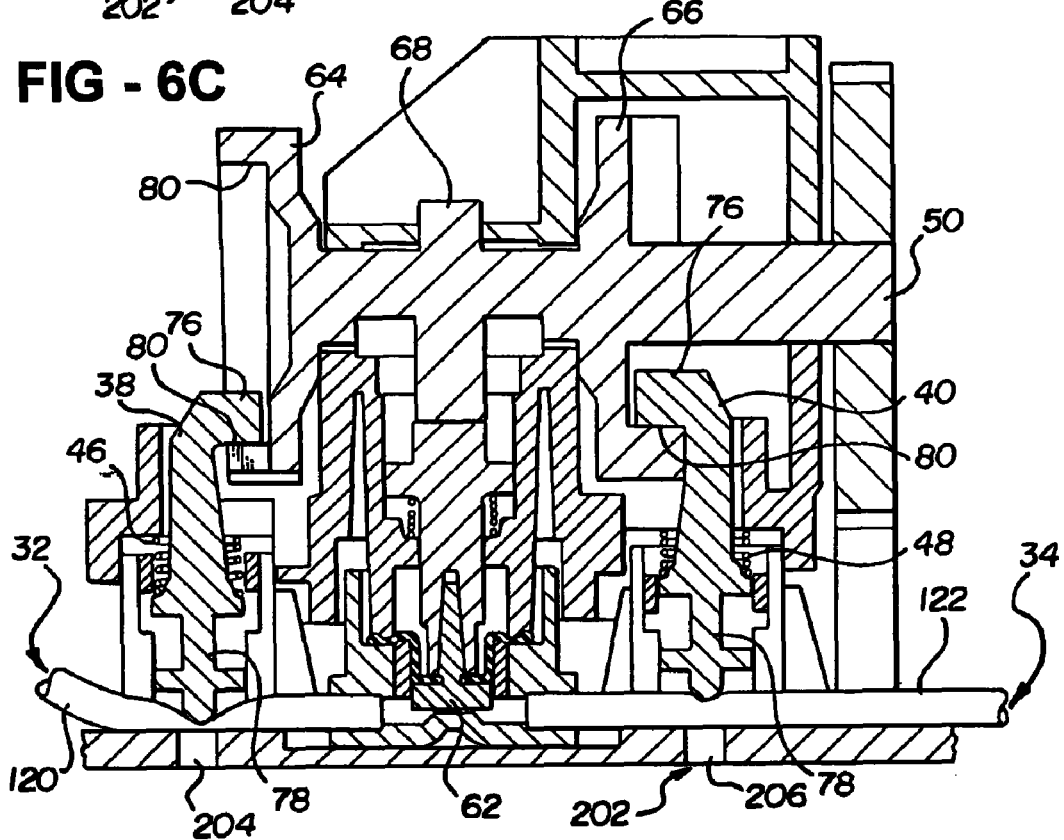
FIG. 6C is a partially cross-sectional side view of the system, as disclosed in FIG. 6A, illustrating the first pinch lever in a closed position and the second pinch lever in an open position to displace medication from the pump assembly.

As FIGS. 6B and 6C disclose, the first pinch lever 38 is moveable between an open position (FIG. 6B) and a closed position (FIG. 6C) to control a flow of the medication into the pump housing 30 through the pump inlet 32, and the second pinch lever 40 is moveable between an open position (FIG. 6C) and a closed position (FIG. 6B) to control a flow of the medication from the pump housing 30 through the pump outlet 34. The pump assembly 28 further includes a motor 42 operatively engaging the first and second pinch levers 38, 40 for moving these levers 38, 40 into the open position such that the medication can be delivered to the patient 12. The motor 42 includes a driving output shaft, not shown in the Figures, for driving the pump assembly 28. A power source 43 is integrated into the system 10 to provide power to the system 10, including the motor 42. Preferably, the power source includes batteries 45 and battery contacts 47.

As shown in FIG. 6A, the first pinch lever 38 is normally-biased to maintain the pump inlet 32 in the closed state and the second pinch lever 40 is normally-biased to maintain the pump outlet 34 in the closed state. To accomplish this, at least one biasing device 44 is included in the pump assembly 28. In one embodiment of the present invention, the at least one biasing device 44 comprises a first 46 and a second 48 compression spring. The first compression spring 46, engages the first pinch lever 38, and the second compression spring 48, engages the second pinch lever 40. As disclosed in FIG. 6A, the first 46 and second 48 compression springs maintain the first and second pinch levers 38, 40 in the closed position during failure of the motor 42 thereby preventing the inadvertent delivery of the medication to the patient 12. More specifically, the closed first pinch lever 38 prevents the medication from being drawn into the pump assembly 28 through the pump inlet 32, and the closed second pinch lever 40 prevents the medication from being displaced from the pump assembly 28 through the pump outlet 34.

Referring primarily to FIGS. 5-6D, to effectively operate the system 10 and move the first and second pinch levers 38, 40 for delivery of the medication to the patient 12, the pump assembly 28 of the present invention further includes a camshaft 50 supported on the pump housing 30. The camshaft 50 is geared to the motor 42, via a number of gears 52, to operatively couple the motor 42 to the first and second pinch levers 38, 40. The camshaft 50 is described in greater detail below.

Figure 7:
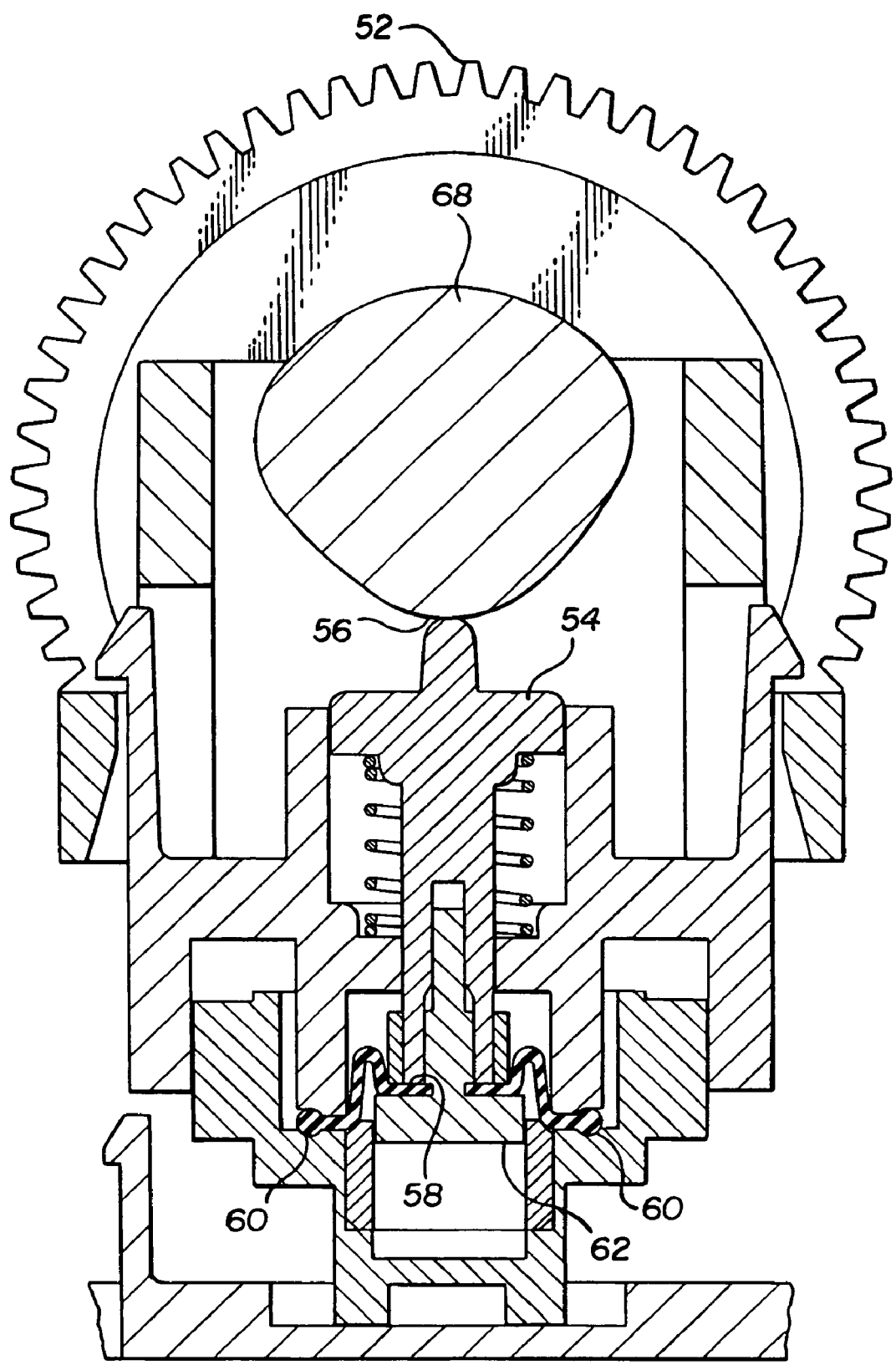
FIG. 7 is a partially cross-sectional side view of the pump assembly.

As disclosed best in FIGS. 5 and 7, the pump assembly 28 also includes a piston 54 disposed in the pump housing 30. The motor 42 moves the piston 54 within the pump housing 30 to draw the medication into the pump housing 30 when the first pinch lever 38 is in the open position and the second pinch lever 40 is in the closed position (see FIG. 6B). The motor 42 also moves the piston 54 within the pump housing 30 to displace the medication from the pump housing 30 when the first pinch lever 38 is in the closed position and the second pinch lever 40 is in the open position (see FIG. 6C). The piston 54 includes an actuation end 56 and a pumping end 58. A diaphragm seal 60 is disposed at the pumping end 58 of the piston 54. The diaphragm seal 60 is secured at the pumping end 58 of the piston 54 by a piston cap 62. The piston 54 also includes at least one slot 63 at the actuation end 56. The at least one detent 36 of the pump housing 30, originally introduced above, engages the at least one slot 63 at the actuation end 56 of the piston 54 to prevent unwanted rotation of the piston 54 as the piston 54 is moved within the pump housing 30 by the motor 42 and the camshaft 50.

The camshaft 50 supports first and second outside cams 64, 66 and an inside cam 68. The inside cam 68 of the camshaft 50 is disposed between the first and second outside cams 64, 66. The first outside cam 64 engages the first pinch lever 38 to move the first pinch lever 38 between the open and closed position, and the second outside cam 66 engages the second pinch lever 40 to move the second pinch lever 40 between the open and closed positions. The inside cam 68 engages the actuation end 56 of the piston 54 to move the piston 54 within the pump housing 30.

Referring to FIG. 5, the first and second outside cams 64, 66 include a plurality of slits 70 along an outer circumference 72 of the cams 64, 66. These slits 70 are used during assembly and testing of the system 10 to confirm dimensional tuning of the cams 64, 66. Also, at least one of the first and second outside cams 64, 66, preferably the first outside cam 64, includes an assembly slot 74 defined within the outer circumference 72 of the cams 64, 66. This assembly slot 74 facilitates assembly of the pump assembly 28. In particular, this assembly slot 74 facilitates mounting of the camshaft 50, including the cams 64, 66, after the first and second pinch levers 38, 40 have already been incorporated into the system 10.

Each of the first and second pinch levers 38, 40 comprise a cam follower 76 and lever guides 78. The lever guides 78 are described below. The cam followers 76 of the pinch levers 38, 40 are engaged by the camshaft 50 for alternating movement of the first and second pinch levers 38, 40 between the open and closed positions such that the medication can be delivered to the patient 12. More specifically, the cam follower 76 of the first pinch lever 38 is engaged by the first outside cam 64 for alternating movement of the first pinch lever 38 between the open and closed positions, and the cam follower 76 of the second pinch lever 40 is engaged by the second outside cam 66 for alternating movement of the second pinch lever 40 between the open and closed positions. Even more specifically, each of the first and second outside cams 64, 66 include internal cam surfaces 80. As disclosed in FIGS. 6A-6D, the cam follower 76 of the first pinch lever 38 rides within the internal cam surface 80 of the first outside cam 64 for alternating movement of the first pinch lever 38, and the cam follower 76 of the second pinch lever 40 rides within the internal cam surface 80 of the second outside cam 66 for alternating movement of the second pinch lever 40.

Referring primarily to FIGS. 3, and 8-10, the system 10 further includes a port assembly 82 that enables various fluids, such as the medication or the sterilization fluid, to flow into, from, and within the system 10. The port assembly 82, hereinafter described as the port 82, extends from the middle housing 20. The port 82 is in fluid communication with the reservoir 24 and the pump assembly 28. During sterilization, the port 82 provides access for the sterilization fluid to flow into the reservoir 24 and the pump assembly 28. During filling, the port 82 provides access for the medication to flow into the reservoir 24 and the pump assembly 28. During delivery of the medication to the patient 12, the port 82 provides access for the medication to be delivered to the patient 12.

Referring particularly to FIGS. 9, and 11A-13B, the port 82 includes an elongated housing 84. The elongated housing 84 includes a proximal end 86, a distal end 88, and an interior wall 90 defining a fluid chamber 92 between the proximal and distal ends 86, 88. It is the proximal end 86 of the elongated housing 84 that extends from the system 10 to provide access for the fluid to flow both into and from the system 10. The port 82 further includes a first fluid connector 94, a second fluid connector 96, and a third fluid connector 98. The first fluid connector 94, alternatively referred to as an outlet of the port 82, extends from the elongated housing 84 to allow the fluid to flow from the fluid chamber 92 into the pump assembly 28. The second fluid connector 96, alternatively referred to as an inlet to the port 82, extends from the elongated housing 84 to allow the fluid to flow from the pump assembly 28 into the fluid chamber 92. The third fluid connector 98, alternatively referred to as an access to the reservoir 24, extends from the elongated housing 84 to allow the fluid to flow between the fluid chamber 92 and the reservoir 24. In the preferred embodiment of the present invention, there are two third fluid connectors 98, one third fluid connector 98 extending from opposite sides of the elongated housing 84.

Figure 11A:
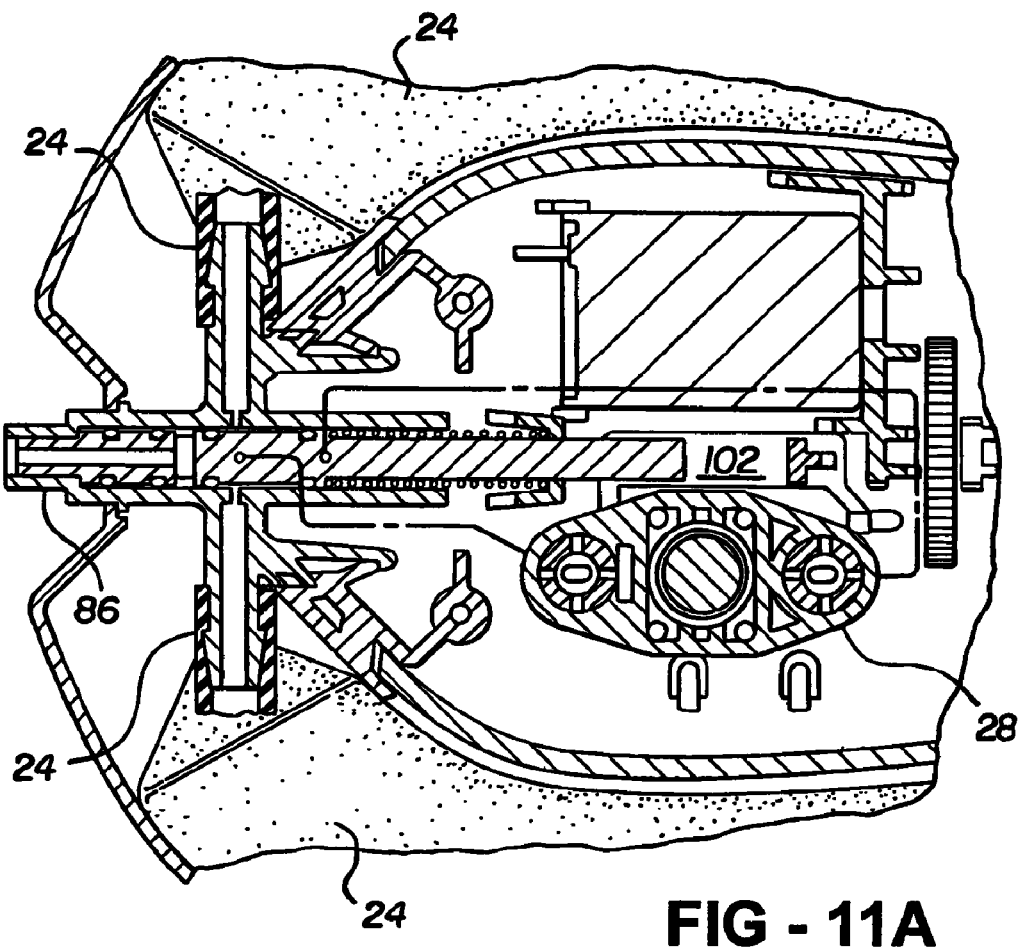
FIG. 11A is a partially cross-sectional top view of the system with the plunger in an off-position.
Figure 11B:
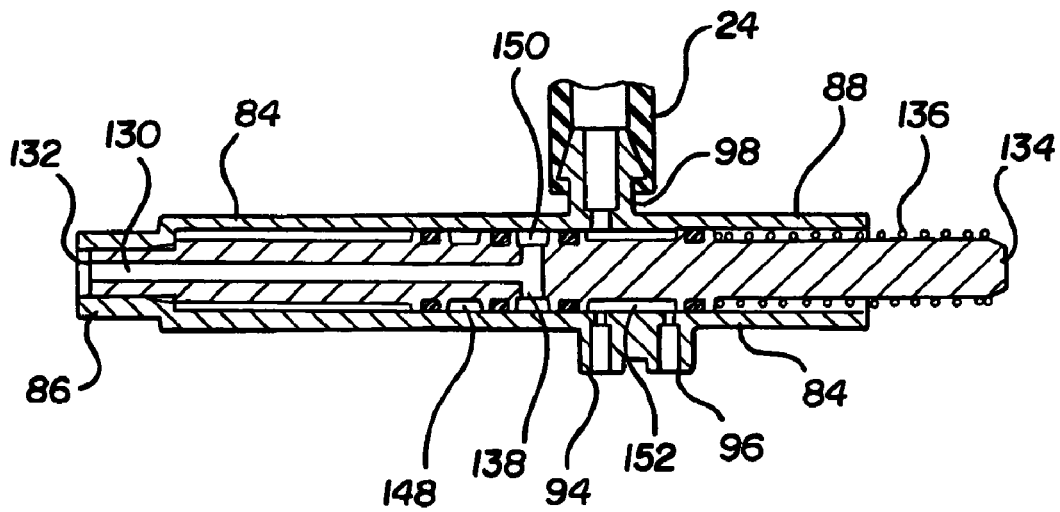
FIG. 11B is a partially cross-sectional view of the port and the plunger disposed in the port in the off-position from FIG. 11A.
Figure 12A:
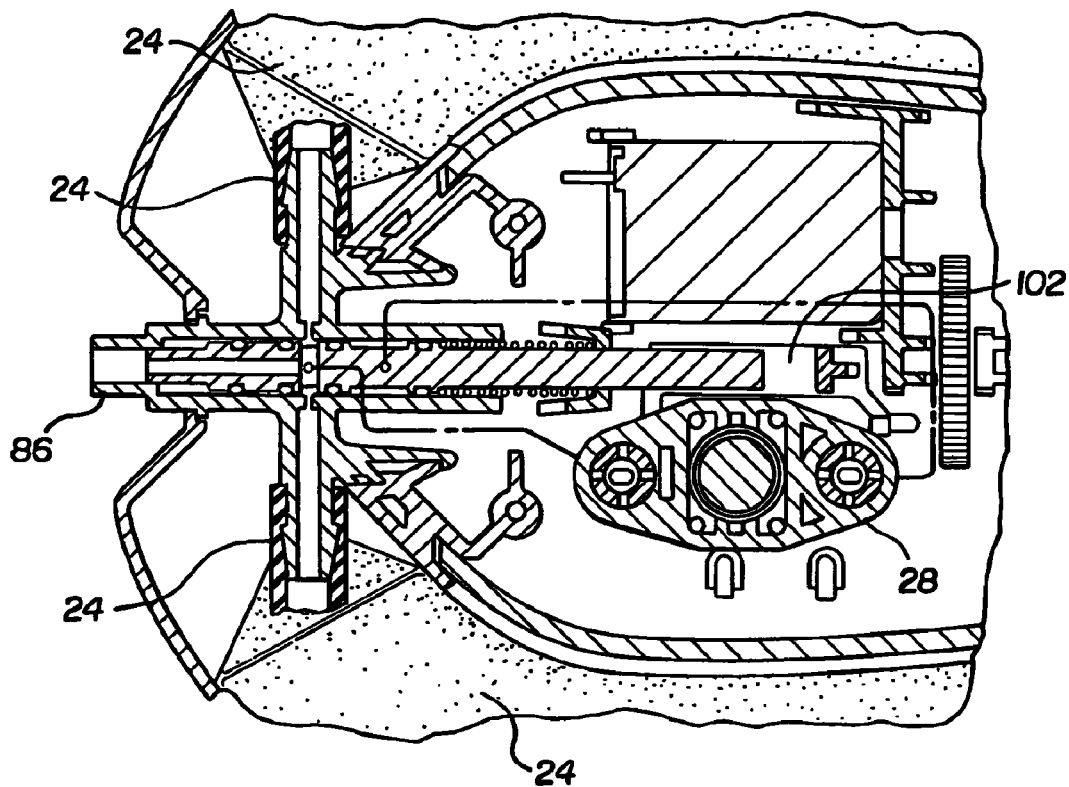
FIG. 12A is a partially cross-sectional top view of the system with the plunger in a fill-position such that the system can be sterilized and filled with medication.
Figure 12B:
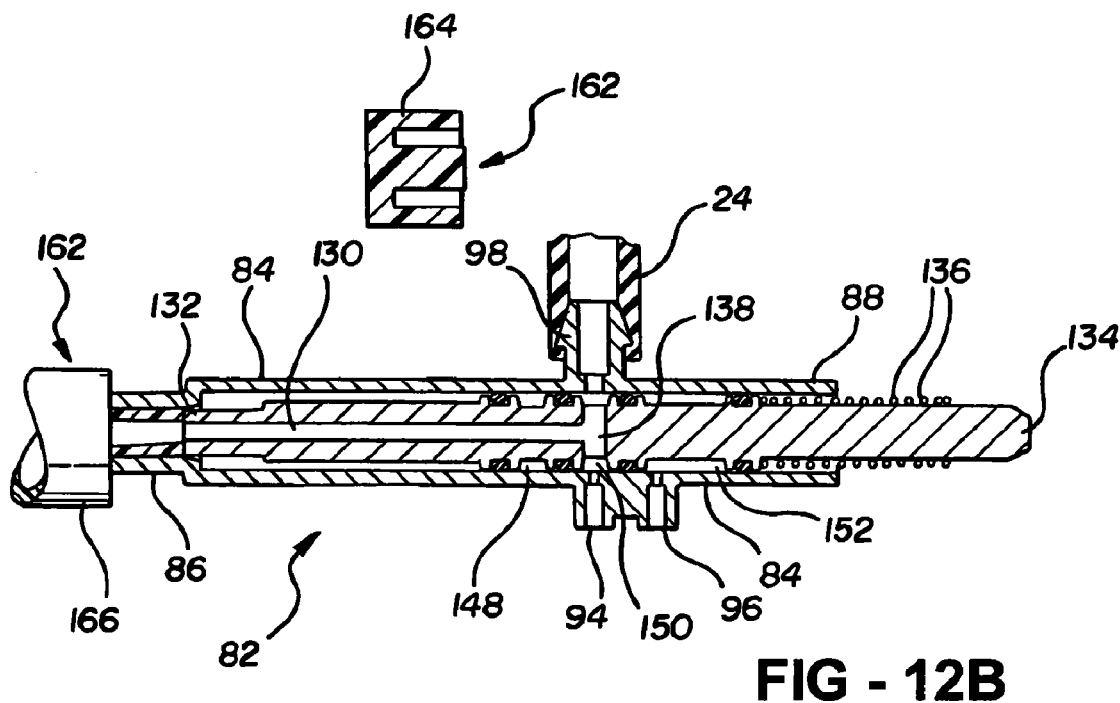
FIG. 12B is a partially cross-sectional view of the port and the plunger disposed in the port in the fill-position from FIG. 12A additionally illustrating a syringe for moving the plunger into the fill-position and a fluid cap for sterilization.
Figure 13A:
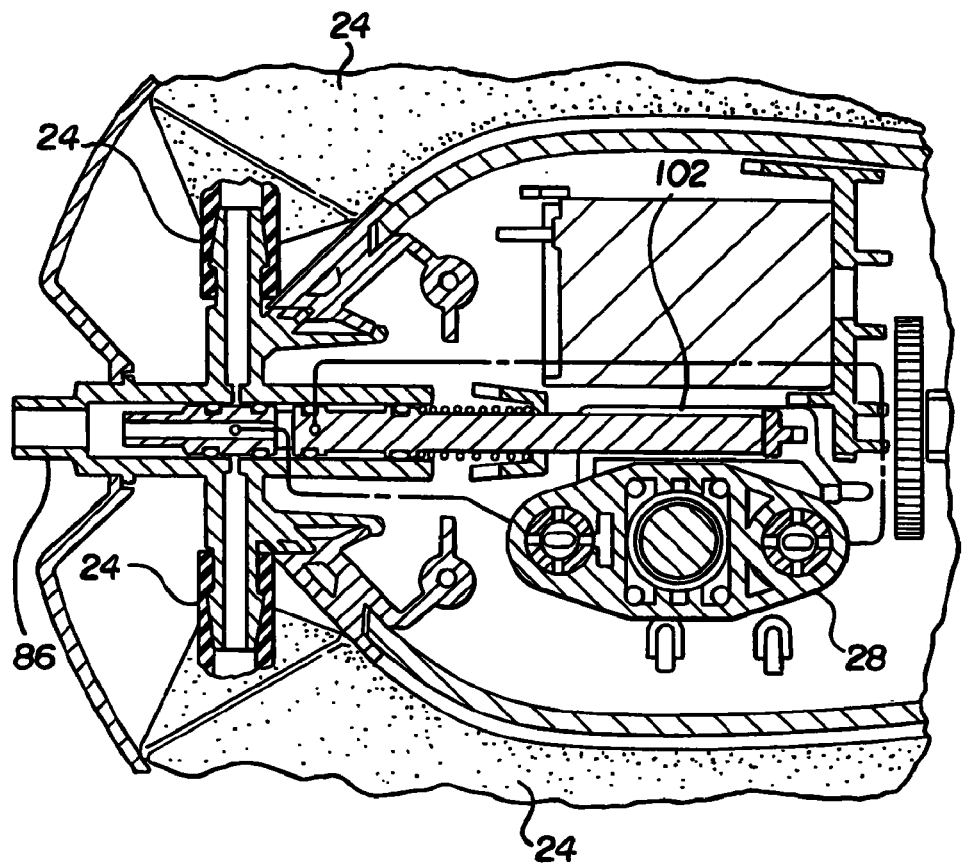
FIG. 13A is a partially cross-sectional top view of the system with the plunger in a fluid delivery-position such that the medication can be delivered to the patient.
Figure 13B:
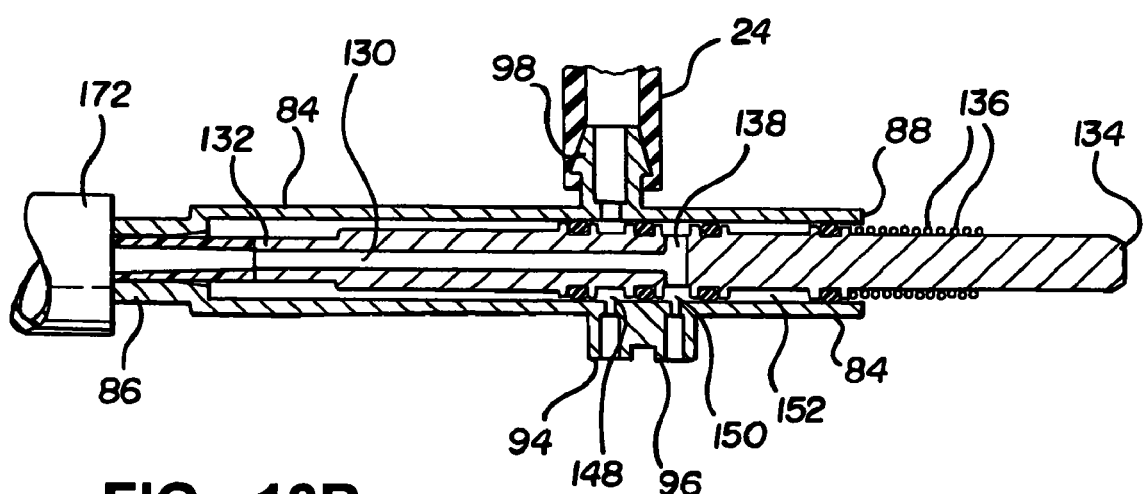
FIG. 13B is a partially cross-sectional view of the port and the plunger disposed in the port in the fluid delivery-position from FIG. 13A additionally illustrating a connector from the infusion tube set.

Referring primarily to FIGS. 3, 6D, 8-10, and 11A-13B, the port 82 further includes a plunger 100. The plunger 100 is disposed in the fluid chamber 92 of the port 82 and is moveable between an off-position (FIGS. 11A-11B), a fill-position (FIGS. 12A-12B), and a fluid delivery-position (FIGS. 13A-13B). As disclosed in FIGS. 11A-11B, in the off-position, the first, second, and third fluid connectors 94, 96, 98 are isolated from the proximal end 86 of the elongated housing 84 by the plunger 100. As a result, the flow of fluid through the port 82 is prevented. As disclosed in FIGS. 12A-12B, in the fill-position, the first and third fluid connectors 94, 98 are in fluid communication with the proximal end 86 of the elongated housing 84. As a result, a fluid flow path, shown but not numbered in FIGS. 12A-12B, is provided between the proximal end 86 of the elongated housing 84, the medication reservoir 24, and the pump assembly 28 such that the fluid can be filled through the proximal end 86 of the housing and into the medication reservoir 24 and the pump assembly 28. This fluid flow path is defined between the port 82, the reservoir 24, and the pump assembly 28 such that the flow of sterilization fluid through the fluid flow path is continuous during sterilization of the system 10. The fill-position of the plunger 100 is utilized when the system 10 is being sterilized with the sterilization fluid and also when the system 10 is being filled with medication. As disclosed in FIGS. 13A-13B, in the fluid delivery position, the first, second, and third fluid connectors 94, 96, 98 are in fluid communication with the proximal end 86 of the elongated housing 84 and with each other for supplying the pump assembly 28 and for delivering the fluid to the patient 12.

Referring particularly to FIGS. 3, and 8-10, the port 82 and the plunger 100 are described in greater detail. The plunger 100 includes a length L, a circumference C, and a plurality of seats 124 disposed along the length L and about the circumference C of the plunger 100. The seats 124 extend outwardly from the circumference C of the plunger 100 to the interior wall 90 of the elongated housing 84 of the port 82 to segregate the fluid chamber 92 of the elongated housing 84. A fluid passage, not numbered, is defined between each of the seats 124 and the interior wall 90 of the housing. These fluid passages control the flow of fluid within the port 82. Although the seats 124 may suitably segregate the fluid chamber 92, it is preferred that seals 126 are disposed about each of the seats 126 to assist with sealing the fluid passages from one another. In the most preferred embodiment these seals are O-rings. At least one leak rib 128 extends at least partially along the interior wall 90 of the elongated housing 84. The at least one leak rib 128 selectively causes at least one of the seals 126 to leak when the plunger 100 is in the fill-position. As disclosed in the Figures, preferably there are two leak ribs 128 that extend along the interior wall 90 of the elongated housing 84.

As shown in FIGS. 11A-13B, the plunger 100 is at least partially hollow. As such, the plunger 100 defines an internal fluid bore 130 that extends within the plunger 100 between the seats 124. The plunger 100 further includes an access end 132 and a plunger actuation end 134. A plunger biasing device 136, preferably a compression spring, is disposed about the plunger actuation end 134 of the plunger 100 to bias the plunger 100 into the off-position. The internal fluid bore 130 extends from the access end 132, where the fluid flows into and from the internal fluid bore 130, toward the plunger actuation end 134. The internal fluid bore 130 includes a fluid duct 138 in fluid communication with one of the fluid passages such that the flow can flow into and from the internal fluid bore 130.

In the most preferred embodiment of the present invention, the plurality of seats 124 are further defined as a first, second, third, and fourth seat 140, 142, 144, 146, respectively. The first seat 140 is disposed toward the access end 132 of the plunger 100, the fourth seat 146 is disposed toward the plunger actuation end 134 of the plunger 100, and the second and third seats 142, 144 are disposed successively between the first and fourth seats 140, 146. In this embodiment, the fluid passages are further defined as a first, second, and third fluid passage 148, 150, 152, respectively. The first fluid passage 148 is defined between the first and second seats 140, 142 and the interior wall 90, the second fluid passage 150 is defined between the second and third seats 142, 144 and the interior wall 90, and the third fluid passage 152 is defined between the third and fourth seats 144, 146 and the interior wall 90.

A first seal 154 is disposed about the first seat 140 for sealing the first fluid passage 148 from the access end 132 of the plunger 100, a second seal 156 is disposed about the second seat 142 for sealing the first and second fluid passages 148, 150 from one another, a third seal 158 is disposed about the third seat 144 for sealing the second and third fluid passages 150, 152 from one another, and a fourth seal 160 is disposed about the fourth seat 146 for sealing the third fluid passage 152 from the plunger actuation end 134 of the plunger 100. In this embodiment, the at least one leak rib 128 extends along the interior wall 90 of the elongated housing 84 from the proximal end 86 toward the distal end 88 just beyond the first seal 154 such that only the first seal 154 selectively leaks when the plunger 100 is in the fill-position.

In this most preferred embodiment, the internal fluid bore 130 extends within the plunger 100 from the access end 132 to the third seat 144. As such, the fluid duct 138 is in fluid communication with the second fluid passage 150 defined between the second and third seats 142, 144 and the interior wall 90 such that the fluid can flow into and from the internal fluid bore 130 at the second fluid passage 150.

The off-, fill-, and fluid delivery-positions of the plunger 100 are now described in the context of this most preferred embodiment having four seats 140, 142, 144, 146, three fluid passages 148, 150, 152, and four seals 154, 156, 158, 160. Referring to FIGS. 11A-11B, when the plunger 100 is in the off-position, the first, second, and third fluid connectors 94, 96, 98 are isolated from the proximal end 86 of the elongated housing 84 and from the access end 132 of the plunger 100 by the first, second, and third seats 140, 142, 144. In this off-position, the first and third fluid connectors 94, 98 are aligned with the third fluid passage 152.

Referring to FIGS. 12A-12B, when the plunger 100 is in the fill-position, the first and third fluid connectors 94, 98 are in fluid communication with the proximal end 86 of the elongated housing 84 and with the access end 132 of the plunger 100 through the second fluid passage 150 and the fluid duct 138 of the internal fluid bore 130. In this fill-position, the first and third fluid connectors 94, 98 are aligned with the second fluid passage 150. As such, the fluid can be filled through the access end 132 of the plunger 100, through the internal fluid bore 130 and the fluid duct 138, and into the reservoir 24 and the pump assembly 28. In the fill-position, the second fluid connector 96 is isolated from the proximal end 86 of the elongated housing 84, from the access end 132 of the plunger 100, and from the first and third fluid connectors 94, 98 by the third and fourth seats 144, 146.

Referring to FIGS. 13A-13B, when the plunger 100 is in the fluid delivery-position, the second fluid connector 96 is in fluid communication with the proximal end 86 of the housing and with the access end 132 of the plunger 100 through said second fluid passage 150 and the fluid duct 138 of the internal fluid bore 130. In the fluid delivery-position, the medication is delivered from the pump assembly 28 to the patient 12. In the fluid delivery-position, the first and third fluid connectors 94, 98 are isolated from the proximal end 86 of the housing and from the access end 132 of the plunger 100 by the first and second seats 140, 142. However, the first and third fluid connectors 94, 98 are in fluid communication with the reservoir 24 through the first fluid passage 148 to supply the pump assembly 28 with the fluid, i.e., with the medication. That is, in the fluid delivery-position, the first and third fluid connectors 94, 98 are aligned with the first fluid passage 148.

A fluid filling device, shown generally in FIG. 12B at 162, engages the proximal end 86 of the housing to automatically move the plunger 100 into the fill-position for filling the reservoir 24 and the pump assembly 28. If the system 10 is being sterilized, then the fluid filling device 162 is preferably a fluid, or sterilization, cap 164 (shown detached from the system 10 in FIG. 12B) that moves the plunger 100 into the fill-position to enable a sterilization fluid to penetrate into the reservoir 24 and the pump assembly 28. The fluid cap 164, by design, automatically moves the plunger 100 into the fill-position. Therefore, when the system 10 is introduced into a chamber filled with the sterilization fluid, preferably EtO gas, then the sterilization fluid flows, or seeps, through the fluid cap 164, through the proximal end 86 of the elongated housing 84 and the access end 132 of the plunger 100, through the internal fluid bore 130 and the fluid duct 138, into the second fluid passage 150, through the third fluid connector 98 into the reservoir 24, and through the first fluid connector 94 into the pump assembly 28.

If the system 10 is being filled with medication, then the fluid filling device 162 is preferably a syringe 166 that moves the plunger 100 into the fill-position for filling the reservoir 24 and the pump assembly 28. The syringe 166 (shown attached to the system 10 in FIG. 12B) engages the access end 132 of the plunger 100 and, by design, automatically moves the plunger 100 into the fill-position for filling the reservoir 24 and the pump assembly 28 through the internal fluid bore 130. Therefore, when the system 10 is being filled, the syringe 166 interacts with the proximal end 86 of the elongated housing 84 and the access end 132 of the plunger 100 and, as the syringe plunger is depressed, the medication flows through the internal fluid bore 130 and the fluid duct 138, into the second fluid passage 150, through the third fluid connector 98 into the reservoir 24, and through the first fluid connector 94 into the pump assembly 28.

To deliver the medication to the patient 12, the system 10 is utilized in combination with the infusion tube set 14. Referring back to FIG. 1A, the infusion tube set 14 includes a fluid end 168 and a patient end 170. The fluid end 168 of the tube set 14, through a delivery connector 172, engages the proximal end 86 of the elongated housing 84 and the access end 132 of the plunger 100 to automatically move the plunger 100 into the fluid delivery-position for delivering the medication to the patient 12. Therefore, as shown in FIGS. 13A-13B, when the pump assembly 28 is operating, the medication is drawn from the reservoir 24 through the third fluid connector 98 into the port 82 at the first fluid passage 148, and through the first fluid connector 94 into the pump inlet 32. The medication is then displaced out of the pump assembly 28 through the pump outlet 34, through the second fluid connector 96 into the port 82 at the second fluid passage 150, through the fluid duct 138 and the internal fluid bore 130 of the plunger 100, and out the access end 132 of the plunger 100 at the fluid end 168 of the infusion tube set 14. From there, the medication flows through the infusion tube set 14, out the patient end 170, and to the patient 12.

Referring primarily to FIGS. 3, 6D, 11A, 12A, 13A, and 14A-14B, the system 10 further includes an actuator 102 disposed in the housing 16. The actuator 102 is moveable between a disengaged position and an engaged position. The disengaged position of the actuator 102 is described below. As disclosed in FIG. 6D, in the engaged position, the actuator 102 operatively engages the pump inlet 32 and the pump outlet 34 to retain, i.e., lock, both the pump inlet 32 and the pump outlet 34 in the open state during sterilization. More specifically, the actuator 102 interacts with the first and second pinch levers 38, 40 to retain both the pump inlet 32 and the pump outlet 34 in the open state during sterilization. In the engaged position, the actuator 102 moves the first pinch lever 38 away from the pump inlet 32 into the open position to retain the pump inlet 32 in the open state, and the actuator 102 moves the second pinch lever 40 away from the pump outlet 34 into the open position to retain the pump outlet 34 in the open state. The actuator 102 retains both the first and second pinch levers 38, 40 in the open position for sterilization despite the bias of the at least one biasing device 44. With the pump inlet 32 and the pump outlet 34 in the open state, the sterilization fluid can penetrate throughout the entire system 10 to completely sterilize the system 10. That is, the sterilization fluid can penetrate into the reservoir 24, the pump inlet 32, the pump housing 30, and the pump outlet 34 to completely sterilize the system 10.

On the other hand, when the actuator 102 is in the disengaged position, as indicated by the absence of the actuator 102 from FIGS. 6B-6C, the actuator 102 is operatively disengaged from the pump inlet 32 and the pump outlet 34. The actuator 102 is in the disengaged position when it is necessary to deliver the medication to the patient 12 such that the pump inlet 32 and the pump outlet 34 can alternate between the open and closed states to deliver the medication the patient 12. Disengagement of the actuator 102 permits the pump inlet 32 and the pump outlet 34 to alternate between the open and closed states.

Figure 14A:
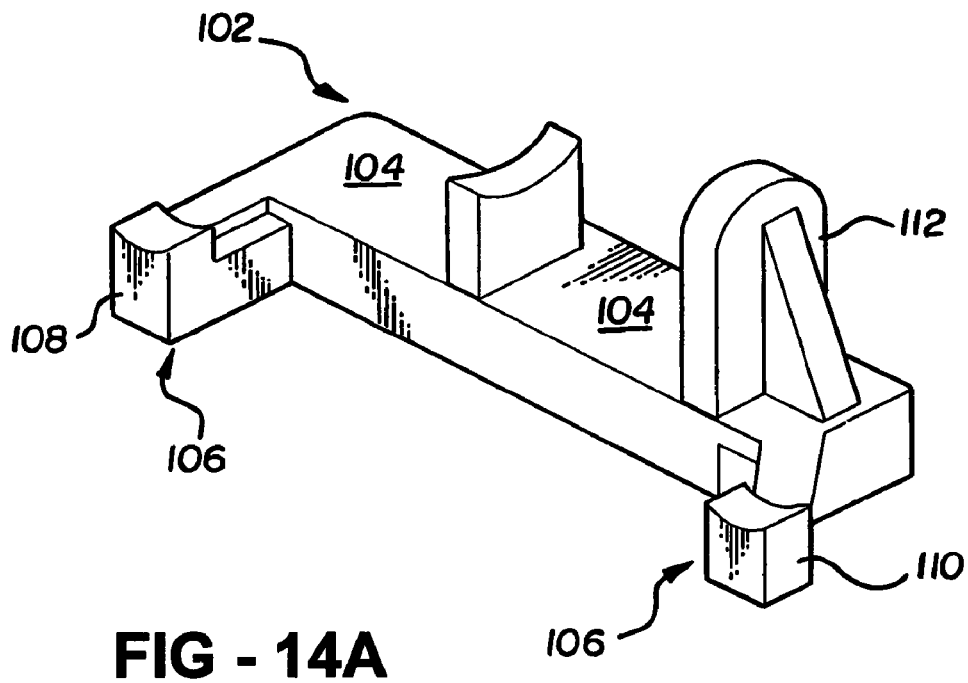
FIG. 14A is an enlarged perspective view of the actuator.
Figure 14B:
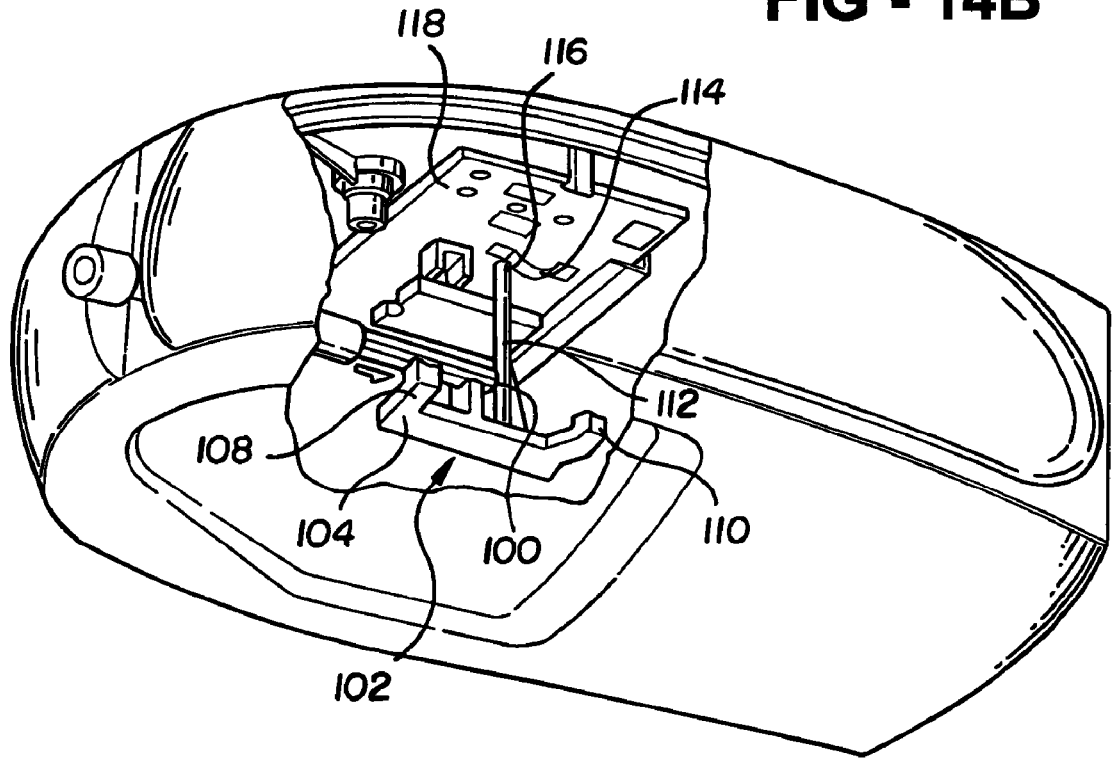
FIG. 14B is a perspective view of an alternative embodiment for the actuator including a control contact disposed at a distal end of an actuation arm.

Referring particularly to FIGS. 14A-14B, the actuator 102 is disclosed in greater detail. The actuator 102 includes a base portion 104 and at least one engagement arm 106 extending from the base portion 104. The at least one engagement arm 106 of the actuator 102 operatively engages the pump assembly 28 to retain the pump inlet 32 and the pump outlet 34 in the open state during sterilization. In the preferred embodiment of the present invention, the actuator 102 more specifically includes first and second engagement arms 108, 110, respectively, extending from the base portion 104. In the preferred embodiment, the actuator 102 also includes an actuation arm 112. The actuation arm 112 extends from the base portion 104 between the first and second engagement arms 108, 110. As shown in the Figures, the actuation arm 112 extends upwardly from the base portion 104 between the first and second engagement arms 108, 110.

During sterilization, the first engagement arm 108 of the actuator 102 engages the first pinch lever 38 to move the first pinch lever 38 away from the pump inlet 32 to retain the pump inlet 32 in the open state. Similarly, during sterilization, the second engagement arm 110 of the actuator 102 engages the second pinch lever 40 to move the second pinch lever 40 away from the pump outlet 34 to retain the pump outlet 34 in the open state.

After sterilization it is desirable to move the actuator 102 into the disengaged position such that the pump assembly 28 can operate and the medication can be delivered to the patient 12. As indicated by the arrow (A) in FIG. 6D, the plunger 100 moves to displace the actuator 102 from the engaged position thereby moving the actuator 102 into the disengaged position. To displace the actuator 102, the plunger 100 engages the actuation arm 112. The plunger 100 displaces the actuator 102 from the operative engagement with the pump assembly 28, after sterilization, such that the pump inlet 32 and the pump outlet 34 can alternate between the open and the closed state to deliver the medication to the patient 12. More specifically, the plunger 100 displaces the actuator 102 from the engagement with the first and second pinch levers 38, 40, after sterilization, such that medication can be delivered to the patient 12. As such, the motor 42, which operatively engages the first and second pinch levers 38, 40, can move these levers 38, 40 for drawing the medication into the pump housing 30 through the pump inlet 32 and for displacing the medication from the pump housing 30 through the pump outlet 34.

Referring now to FIG. 14B, a control contact 114, preferably a spring-like control contact 114, may be disposed at a distal end 116 of the actuation arm 112 away from the base portion 104 to indicate to the system 10 whether the actuator 102 is in the engaged or the disengaged position. The control contact 114 interacts with the actuation arm 112 of the actuator 102 upon the movement of the actuator 102 between the engaged or the disengaged position. If the control contact 114 is included, it is preferred that when the actuator 102 is disengaged from the first and second pinch levers 38, 40, i.e., when the actuator 102 is in the disengaged position, it contacts the control contact 114 to active an electronic controller 118. The electronic controller 118 is activated to permit the pump assembly 28 to operate to deliver the medication to the patient 12. As indicated above, it is preferred that the actuation arm 112 of the actuator 102 is in contact with the control contact 114 when the actuator 102 is in the disengaged position. Of course, it is to be understood that the opposite could be true. That is, the system 10 can be designed such that the actuation arm 112 of the actuator 102 is in contact with the control contact 114 when the actuator 102 is in the engaged position.

The system 10 further includes a medication inlet tube 120 and a medication outlet tube 122. The medication inlet tube 120 is connected between the port 82 and the pump inlet 32 to provide access for the sterilization fluid to flow from the port 82 into the pump assembly 28, specifically into the pump inlet 32. The medication outlet tube 122 is connected between the pump outlet 34 and the port 82 to provide access for the sterilization fluid to flow from the pump assembly 28, specifically from the pump outlet 34, into the port 82. The medication inlet tube 120 and the first pinch lever 38 together establish the pump inlet 32, and the medication outlet tube 122 and the second pinch lever 40 together establish the pump outlet 34.

When the at least one biasing device 44 engages the first pinch lever 38 to normally-bias the first pinch lever 38 into the closed position, the medication inlet tube 120 is pinched. As such, the pump inlet 32 is maintained in the closed state. Similarly, when the at least one biasing device 44 engages the second pinch lever 40 to normally-bias the second pinch lever 40 into the closed position, the medication outlet tube 122 is pinched. As such, the pump outlet 34 is maintained in the closed state. However, as disclosed in FIG. 6D, when the actuator 102 is in the engaged position during sterilization, the actuator 42 overcomes the bias of the at least one biasing device 44 to move the first pinch lever 38 away from the medication inlet tube 120 such that the pump inlet 32 remains in the open state, and the actuator 102 overcomes the bias of the at least one biasing device 44 to move the second pinch lever 40 away from the medication outlet tube 122 such that the pump outlet 34 remains in the open state.

Referring back to FIG. 4, the system 10 further includes the electronic controller 118. The electronic controller 118 controls an amount of the medication that is to be delivered to the patient 12 by controlling the pump assembly 28 as described further below. The electronic controller 118 is mounted to a printed circuit board 119 that is attached to the cover 122. Furthermore, the electronic controller 118 remains mounted to the cover 22 during sterilization such that the entire system 10, including all mechanical components, the reservoir 24, and the electronic controller 118, is simultaneously sterilized. An electronic display 174 and an input device 176, in the form of at least one control button 176, are mounted in the cover 22. The electronic display 174 and the input device 176 are in electronic communication with the electronic controller 118 to control the amount of the medication to be delivered to the patient 12. As with the electronic controller 118, the electronic display 174 and the input device 176 also remain in the housing 16 during sterilization.

Figure 15A:
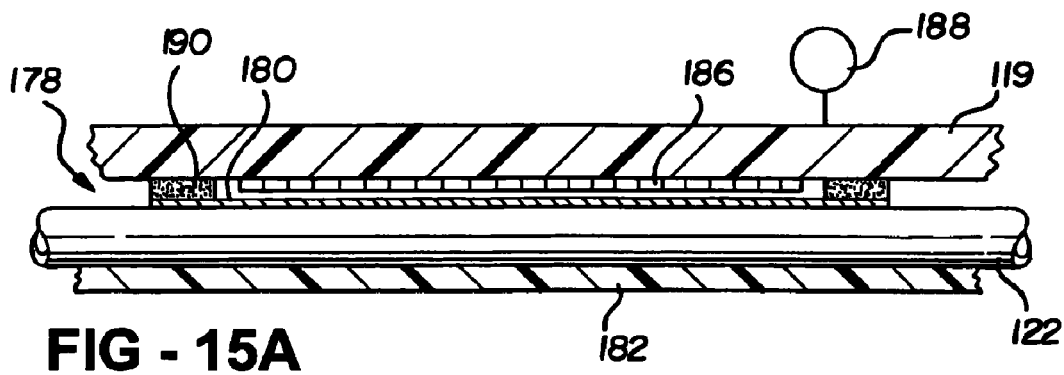
FIG. 15A is a partially cross-sectional side view of a blockage detection system according to the present invention when the medication outlet tube is in a normal condition.
Figure 15B:
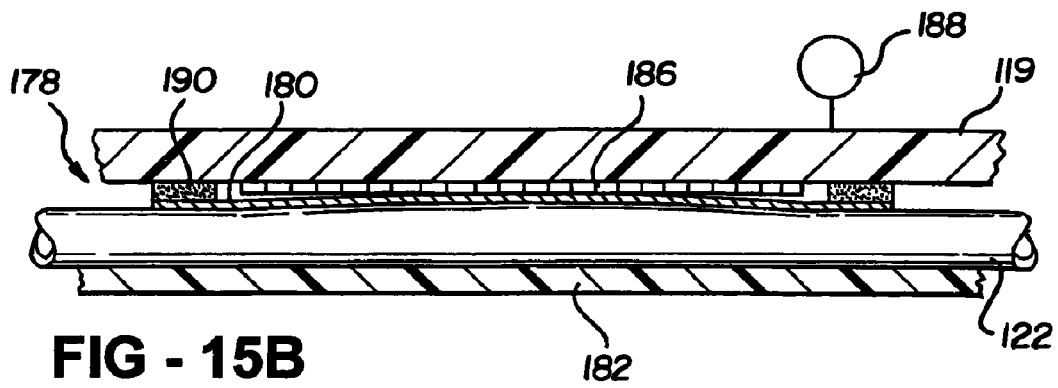
FIG. 15B is a partially cross-sectional side view of the blockage detection system of FIG. 15A when the medication outlet tube is in an expanded condition due to a blockage.

The present invention also provides a blockage detection system, which is generally disclosed at 178 in FIGS. 15A-15B. The blockage detection system 178 detects a blockage in the flow of the medication to the patient 12. The blockage detection system 178 comprises the housing 16, the reservoir 24, the port 82, the pump assembly 28, the medication outlet tube 122, and the electronic controller 118. The blockage detection system 178 also includes a detection film 180 which is described below.

In the blockage detection system 178, the printed circuit board 119 is mounted to the cover 22. A portion of the outlet tube 122 is mounted adjacent to the printed circuit board 119 to be exposed to the detection film 180, which is disposed on the printed circuit board 119. The outlet tube 122 fluidly connects the pump assembly 28 and the port 82 to provide access for the medication to flow from the pump assembly 28 into the port 82 and to the patient 12. The outlet tube 122 has a diameter that is contractible and expandable between a normal condition (see FIG. 15A) and an expanded condition (see FIG. 15B). The diameter of the outlet tube 122 contracts and expands in response to variations in pressure that result from the flow of the medication from the reservoir 24 through the pump assembly 28 into the port 82 and to the patient 12.

Figure 16:
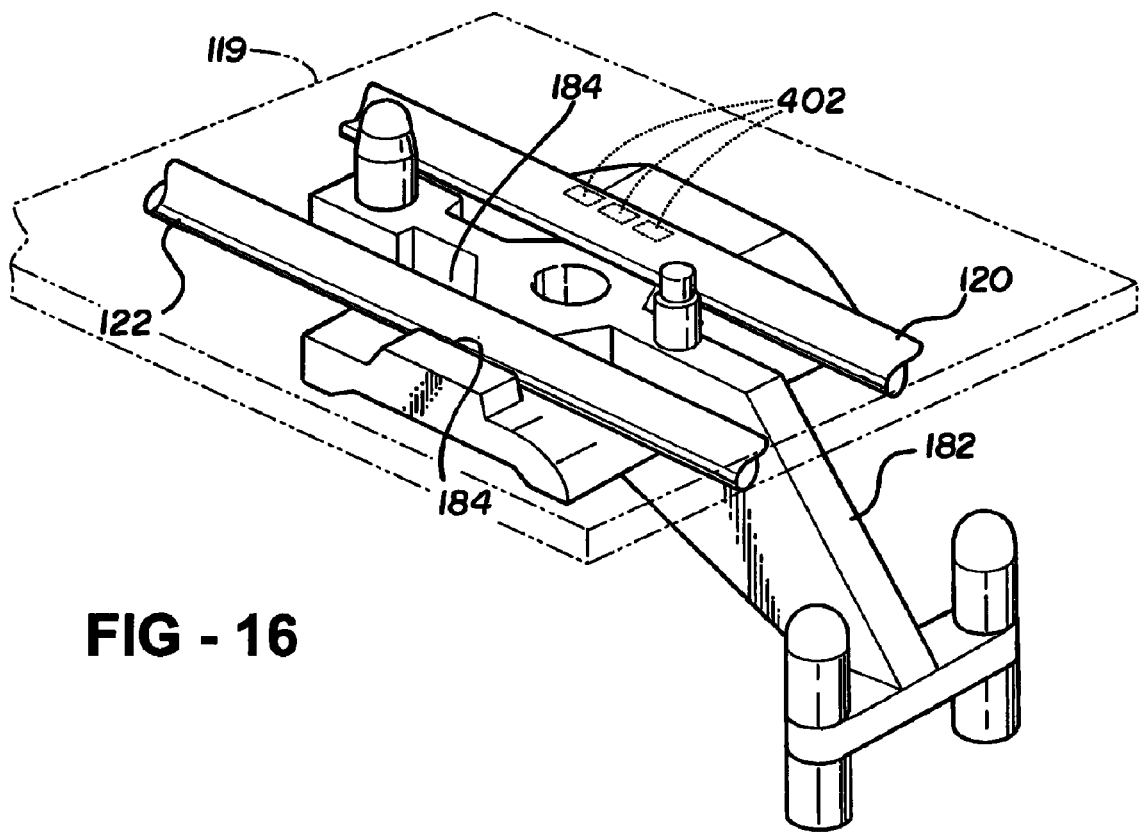
FIG. 16 is a perspective view of a support platform with the medication inlet and outlet tubes.

As disclosed in the Figures, the outlet tube 122 is placed in contact with the detection film 180 via a support platform 182 (see FIG. 16). That is, the support platform 182 is mounted to the middle housing 20 and the printed circuit board 119 to support the outlet tube 122 adjacent to the detection film 180 on the printed circuit board 119. The support platform 182 includes at least one tube slot 184. The at least one tube slot 184 houses the diameter of the outlet tube 122. The outlet tube 122 is mounted in the tube slot 184 such that the portion of the outlet tube 122 is exposed to the detection film 180.

The detection film 180 is disposed between the printed circuit board 119 and the outlet tube 122. The detection film 180 is in contact with the portion of the outlet tube 122 and remains spaced from the printed circuit board 119 when the diameter of the outlet tube 122 is in the normal condition, as in FIG. 15A. On the other hand, the detection film 180 is in contact with the outlet tube 122 and contacts the printed circuit board 119 when the diameter of the outlet tube 122 is in the expanded condition, as in FIG. 15B, in response to increased pressure resulting from the blockage in the flow of the medication to the patient 12. More specifically, it is preferred that an electronic switch 186 is embedded in the printed circuit board 119 for contact by the detection film 180. The detection film 180 interacts with the electronic controller 118 by contacting the electronic switch 186 to transmit a corresponding signal to the electronic controller 118 when the diameter of the outlet tube 122 is in the expanded condition.

For activating the electronic controller 118 when the diameter of the outlet tube 122 is in the expanded condition, it is also preferred that the detection film 180 is conductive. Once activated by the detection film 180, the electronic controller 118 deactivates the pump assembly 28 to prevent delivery of the medication to the patient 12 when the diameter of the outlet tube 122 is in the expanded condition. Deactivation of the pump assembly 28 prevents further blockage and further increases in pressure. To properly ensure that the there is a blockage in the outlet tube 122, it is most preferred that the electronic controller 118, and therefore the pump assembly 28, are deactivated only if the diameter of the outlet tube 122 is in the expanded condition for more than at least one or two cycles of the pump assembly 28. This additional measure avoids false readings and the deactivation of the pump assembly 28 when the outlet tube 122 is truly not blocked.

Additionally, once activated by the detection film 180, the electronic controller 118 may also activate an alarm 188, shown schematically in the Figures. The alarm 188, which can be audible and/or visually displayed on the electronic display 174, would indicate the blockage that is due to the blockage in the flow of the medication to the patient 12.

It is preferred that the detection film 180 is mounted to the printed circuit board 119 with an adhesive layer 190. The adhesive layer 190 also establishes a thickness that is necessary to space the detection film 180, specifically a portion of the detection film 180, from the electronic switch 186 when the diameter of the outlet tube 122 is in the normal condition. The detection film 180 contacts the electronic switch 186 to activate the electronic controller 118 when the diameter of the outlet tube 122 is in the expanded condition in response to increased pressure in the outlet tube 122.

Figure 17:
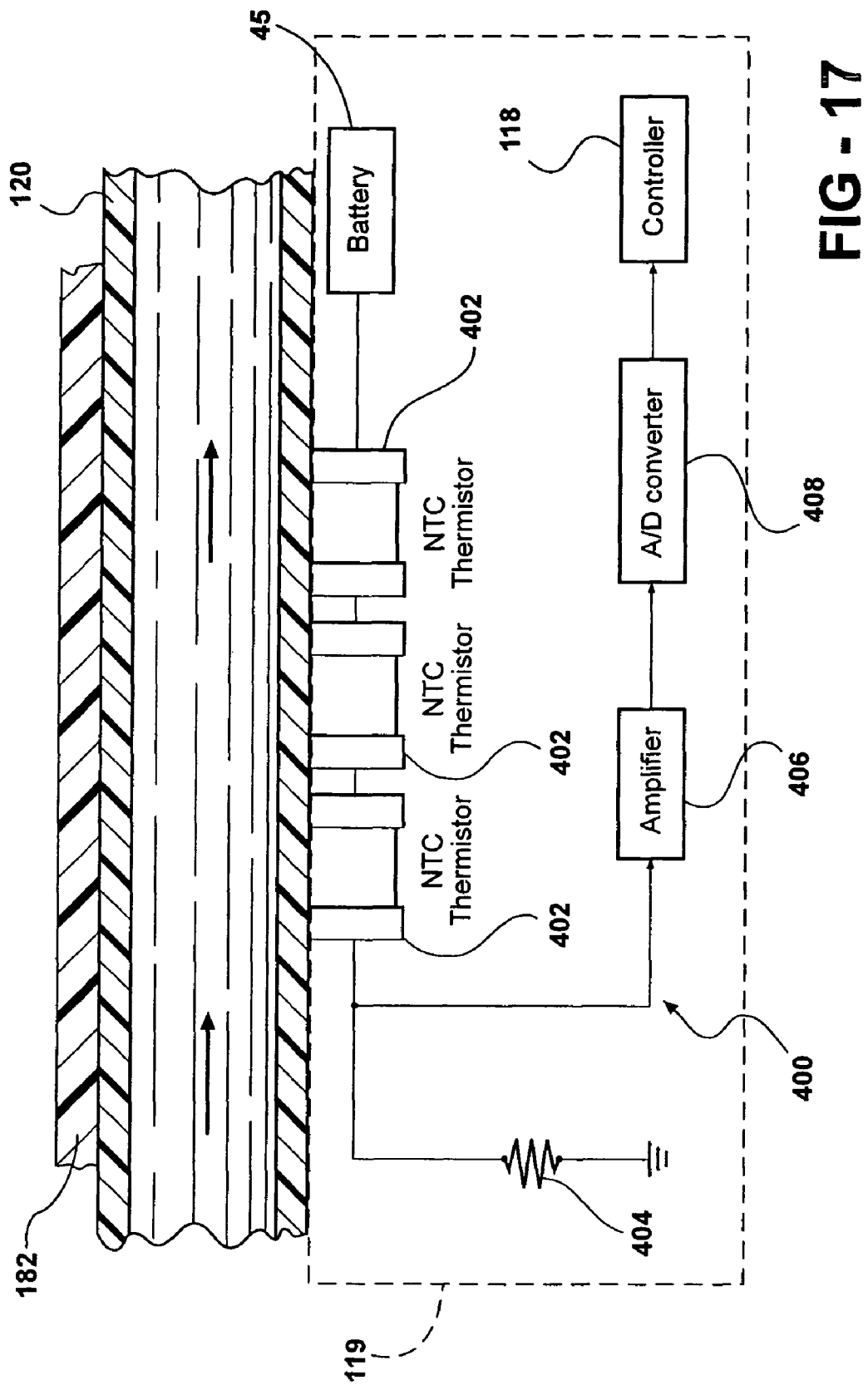
FIG. 17 is a schematic view of an empty detection system of the present invention.
Figure 18A:
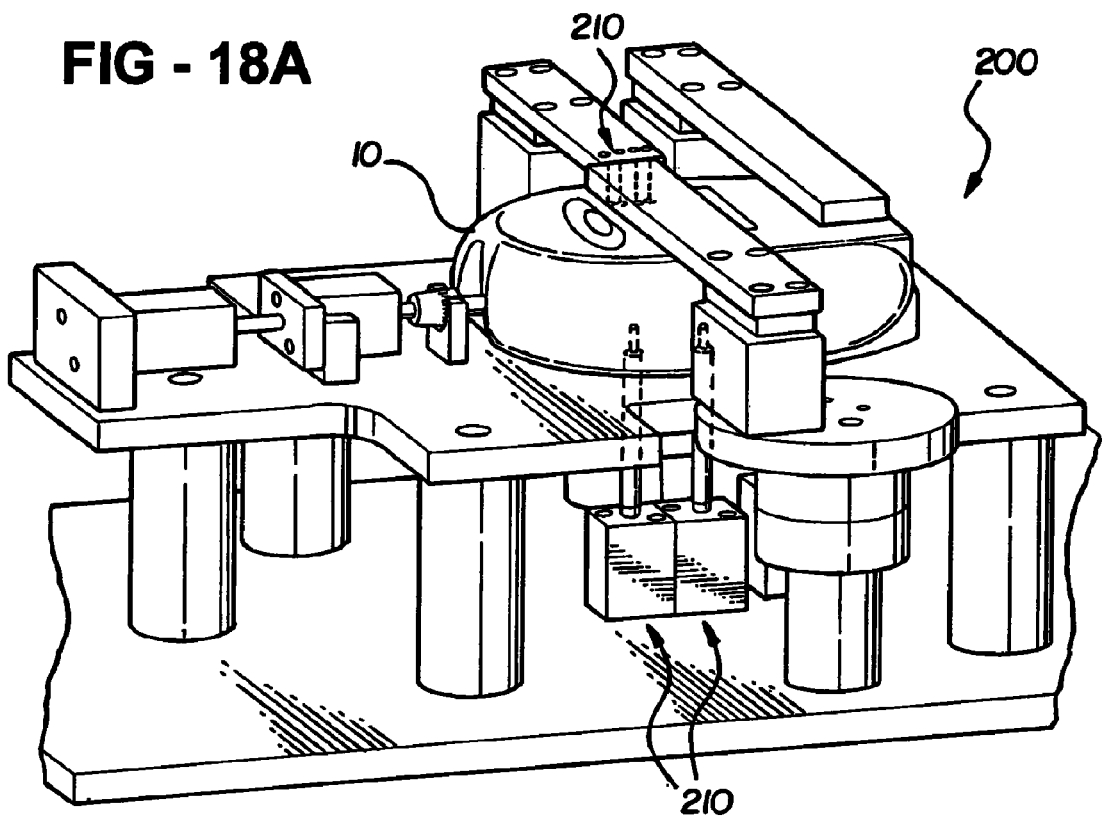
FIG. 18A is a top perspective view of the system engaged with a testing instrument for confirming proper operation of the system after assembly and prior to use.
Figure 18B:
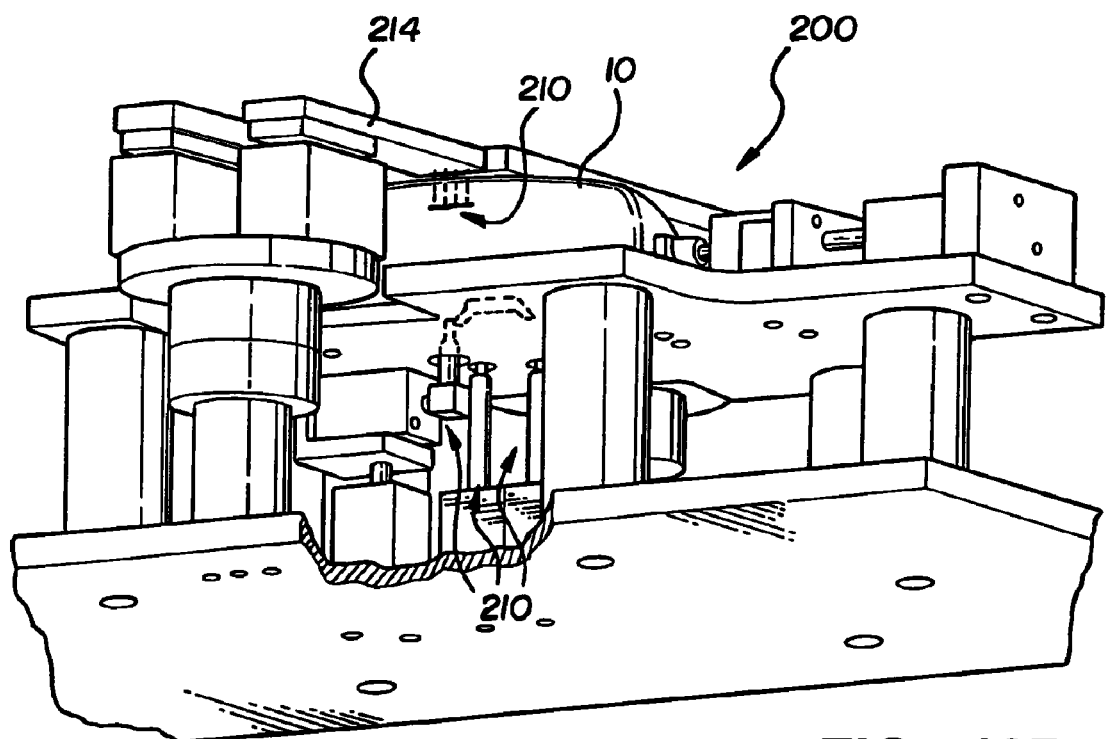
FIG. 18B is a bottom perspective view of the system engaged with a second testing instrument for confirming proper operation of the system after assembly and prior to use.

Referring to FIG. 17, an empty detection system 400 is also provided for the system 10. The empty detection system 400 determines when a supply of the medication has been depleted. The empty detection system 400 comprises a detection circuit including a plurality of thermal elements 402, preferably three negative temperature coefficient (NTC) thermistors 402, preferably positioned on the printed circuit board 119 and thermally coupled with at least a portion of the inlet tube 120 (it should be appreciated that the thermistors 402 may also be separate from the printed circuit board 119, as with all electronic components disclosed as being positioned on the printed circuit board 119). In other embodiments, the thermistors 402 can be thermally coupled to the outlet tube 122. The power source, e.g, the battery 45, powers the thermistors 402 to alter their temperature, e.g., heat, the thermistors 402 during use. Referring to FIG. 16, the portion of the inlet tube 120 is thermally coupled to the thermistors 402 on the printed circuit board 119 via the support platform 182. That is, the support platform 182 is mounted to the middle housing 20 and the printed circuit board 119 to support the inlet tube 120 adjacent to the thermistors 402 on the printed circuit board 119. The support platform 182 includes at least one tube slot 184. The at least one tube slot 184 houses the diameter of the inlet tube 120. The inlet tube 120 is mounted in the tube slot 184 such that the portion of the inlet tube 120 is exposed to the thermistors 402.

Referring back to FIG. 17, prior to fluid flowing through the inlet tube 120, i.e., in a first condition of the pump assembly 28 such as when the pump assembly 28 is not operating, a voltage is applied across the thermistors 402 and a voltage dividing resistor 404 by the battery source 45, such as 4.5 volts. The thermistors 402 are connected in series with the voltage dividing resistor 404. The current flowing through the thermistors 402 causes them to self-heat, thereby causing a decrease in resistance and an increase in voltage observed across the voltage dividing resistor 404 (it should be appreciated that depending on the type of thermistor used, the decrease in resistance and increase in voltage may be reversed). An amplifier 406 amplifies the voltage and sends a corresponding amplified signal to an analog-to-digital converter 408, which then sends a corresponding digital signal to the controller 118 for processing (specifically by a processor of the controller 118). The controller 118 records a first value of the voltage, or other measurable electrical parameter, as provided by the analog-to-digital converter 408, and stores it in a memory of the controller 118.

The heat from the thermistors 402 increases the temperature of the medication inlet tube 120 and fluid near the thermistors 402. When the pump assembly 28 begins operating, i.e., in a second condition of the pump assembly 28, the heated fluid near the thermistors 402 is replaced with unheated fluid as fluid flows through the inlet tube 120, which draws heat away from the thermistors 402. This cooling effect increases the resistance of the thermistors 402, which decreases the voltage observed across the voltage dividing resistor 404. The controller 118 then records a second value of the voltage or other measurable electrical parameter, as provided by the analog-to-digital converter 408, and compares the second value to the first value to determine a change, or drop, in voltage.

As the reservoir 24 becomes empty, the cooling effect is reduced, i.e., less fluid is carrying away heat from the medication inlet tube 120 adjacent to the thermistors 402, and the observed voltage drop lessens. Below a predetermined voltage threshold, or voltage drop, the system 10 is deemed empty by the controller 118. When the system 10 is determined to be empty, the controller 118 produces a signal which causes an empty symbol (not shown), such as a conventional automotive fuel gauge, to be displayed on the display 174. Fluid can then be added to the reservoir through a refill port 300, as described further below.

Referring now to FIGS. 1B, 6A-6D, and 18A-18B, the system 10 of the present invention can be tested using a testing instrument 200 after assembly of the system 10. The system 10 is tested after assembly and prior to shipment and use by the surgeons, patients, and the like to confirm various operations of the system 10. In the preferred embodiment, to test the system 10, the system 10 is mounted onto the testing instrument 200. One operation of the system 10 that is confirmed after assembly of the system 10 is the operation of the pump assembly 28.

To confirm these operations, the system 10 includes at least one testing access port 202. The at least one testing access port 202 is defined within the base 18 and is aligned with at least one of the pump inlet 32, the pump outlet 34, and the actuator 102. Preferably, the at least one testing access port 202 is aligned with all three of the pump inlet 32, the pump outlet 34, and the actuator 102. The at least one testing access port 202 provides access for the testing instrument 200 to move the actuator 102 between the disengaged position and the engaged position. If the at least one testing access port 202 is aligned with the pump inlet 32 and the pump outlet 34 then it is aligned with the first and second pinch levers 38, 40, respectively. Also, as for the alignment with the actuator 102, the at least one testing access port 202 is more specifically aligned with the at least one engagement arm 106 of the actuator 102. This provides access for the testing instrument 200 to move the actuator 102 between the disengaged position and the engaged position.

The system 10 is preferably assembled with the actuator 102 in the engaged position such that the first and second pinch levers 38, 40 are in the open position and the resiliency and life of the medication inlet and outlet tubes 120, 122 is not compromised. Because the at least one testing access port 202 provides access for the testing instrument 200 to move the actuator 102 between the disengaged position and the engaged position, the testing instrument 200 can be inserted into the at least one testing access port 202 to disengage the actuator 102, i.e., to move the actuator 102 into the disengaged position. As such, the pump inlet 32 and the pump outlet 34 can alternate between the open and closed states after assembly and during testing of the system 10.

The at least one testing access port also provides access for the testing instrument 200 such that the pump inlet 32 and the pump outlet 34 can be retained in the open state after the system 10 has been tested to prepare the system 10 for sterilization. That is, after the system 10 has been tested, the actuator 102 is moved from the disengaged position back into the engaged position to prepare the system 10 for sterilization. In the engaged position, the first and second pinch levers 38, 40 are retained in the open state.

In the preferred embodiment, the at least one testing access port 202 is further defined as first, second, and third testing access ports 204, 206, 208, respectively. The first testing access port 204 is aligned with the pump inlet 32, the second testing access port 206 is aligned with the pump outlet 34, and the third testing access port 208 is aligned with the actuator 102 for providing access to the testing instrument 200 to move the actuator 102 into the engaged position. More specifically, the first testing access port 204 is aligned with the first pinch lever 38 such that the first pinch lever 38 is engaged by the testing instrument 200. Once inside the first testing access port 204, the testing instrument 200 forces the first pinch lever 38 away from the pump inlet 32 and forces the pump inlet 32 into the open state. Similarly, the second testing access port 206 is aligned with the second pinch lever 40 such that the second pinch lever 40 is engaged by the testing instrument 200. Once inside the second testing access port 206, the testing instrument 200 forces the second pinch lever 40 away from the pump outlet 34 and forces the pump outlet 34 into the open state. The first and second pinch levers 38, 40 include the lever guides 78 opposite the cam follower 76 of each pinch lever 38, 40. To move the first and second pinch levers 38, 40, the testing instrument 200 engages the lever guides 78 upon insertion into the first and second testing access ports 204, 206. After the testing instrument 200 forces the first and second pinch levers 38, 40 away from the pump inlet 32 and the pump outlet 34, respectively, the testing instrument 200 is introduced into the third testing access port 208 and the actuator 102 is moved into the engaged position to engage and retain the pinch levers 38, 40 in the open position such that the system 10 is now prepared for sterilization. It is to be understood by those skilled in the art that the testing instrument 200 includes male prongs, generally indicated at 210, introduced into the testing access ports 204, 206, 208.

The system 10 further includes at least one controller access port 212 defined within the base 16. In the preferred embodiment, the at least one controller access port 212 is defined within the top housing 22 or cover. The at least one controller access port 212 is aligned with the electronic controller 118 to provide access for a second testing instrument 214. It is to be understood that the second testing instrument 214 and the testing instrument 200 may be a unitary component, as disclosed in the Figures. The second testing instrument 214 causes the electronic controller 118 to activate the motor 42 such that the motor 42 is powered to alternate the pump inlet 32 and the pump outlet 34 between the open and closed states after assembly and during testing of the system 10. The second testing instrument 214 also preferably includes male prongs 210 that are introduced into the controller access ports 212.

Referring primarily to FIGS. 2A-3, and 19-20, the system 10 of the present invention is also suitable to be carried by the patient 12. To facilitate carrying of the system 10 so the patient 12 can remain ambulatory, a carrying strap 216 is mounted within the base 18 for the carrying of the system 10 by the patient 12. An integral storage cavity 218 is defined within the base 18. The carrying strap 216 is at least partially disposed in the integral storage cavity 218. The carrying strap 216 at least partially extends from the integral storage cavity 218 to interact with the patient 12 for carrying the system 10.

Figure 20:
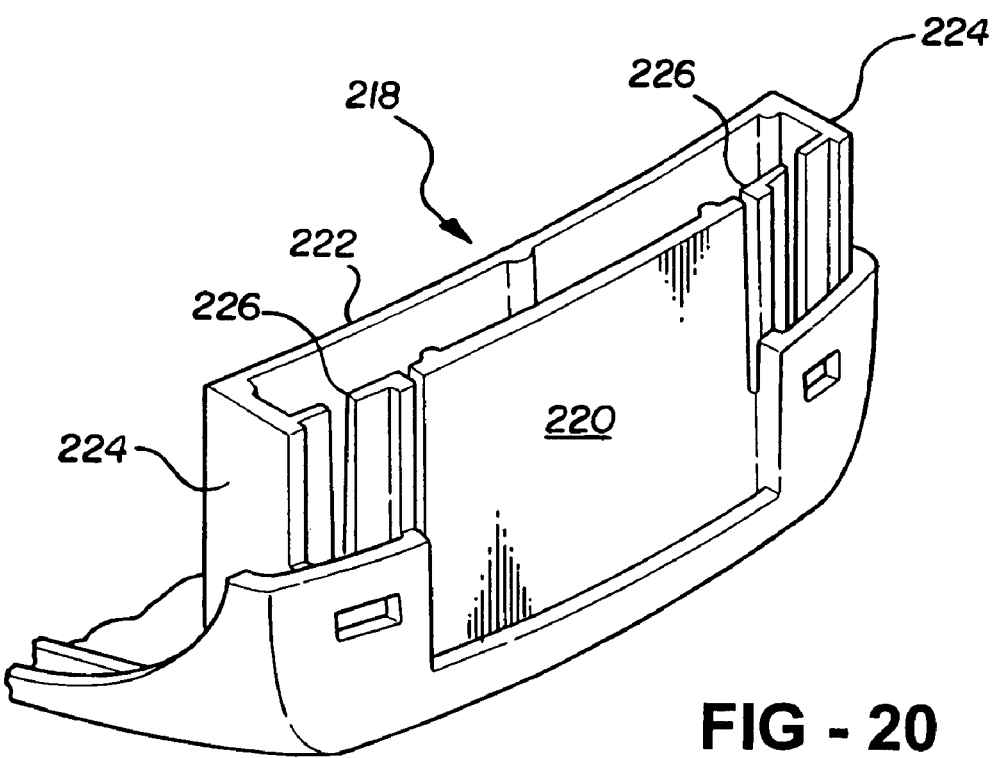
FIG. 20 is an enlarged top perspective view of the integral storage cavity defined within the base of the system.

The system 10 further includes a plurality of cavity walls. The cavity walls extend from the base 18 to define the integral storage cavity 218 between the base 18 and cover 22. Referring particularly to FIG. 20, the cavity walls are further defined as a front wall 220, a rear wall 222, and first and second side walls 224 extending between the front and rear walls 220, 222 to support the front and rear walls 220, 222 and to define the integral storage cavity 218. At least one strap slot 226 is defined within the front wall 220 such that at least a portion, not numbered, of the carrying strap 216 extends from the integral storage cavity 218 and through the strap slot 226. The patient 12 can then access the portion of the carrying strap 216 when desired.

In interacting with the carrying strap 216, the patient 12 simply manipulates, or grabs, the portion of the carrying strap 216 to pull a length of the carrying strap 216 from the integral storage cavity 218. This length is then looped about the head of the patient 12 as specifically disclosed in FIG. 19. In the preferred embodiment, the carrying strap 216 is retractable into the integral storage cavity 218 after the length has been pulled from the integral storage cavity 218 by the patient 12. The system 10 further includes a clip 228 that connects opposing ends of the carrying strap 216 such that the carrying strap 216 is adjustable to fit patients 12 of all sizes. In the most preferred embodiment of the present invention, which is disclosed in FIG. 19, the carrying strap 216 is further defined as a shoulder strap. The shoulder strap suspends from a shoulder of the patient 12 for carrying the system 10.

Figure 1:
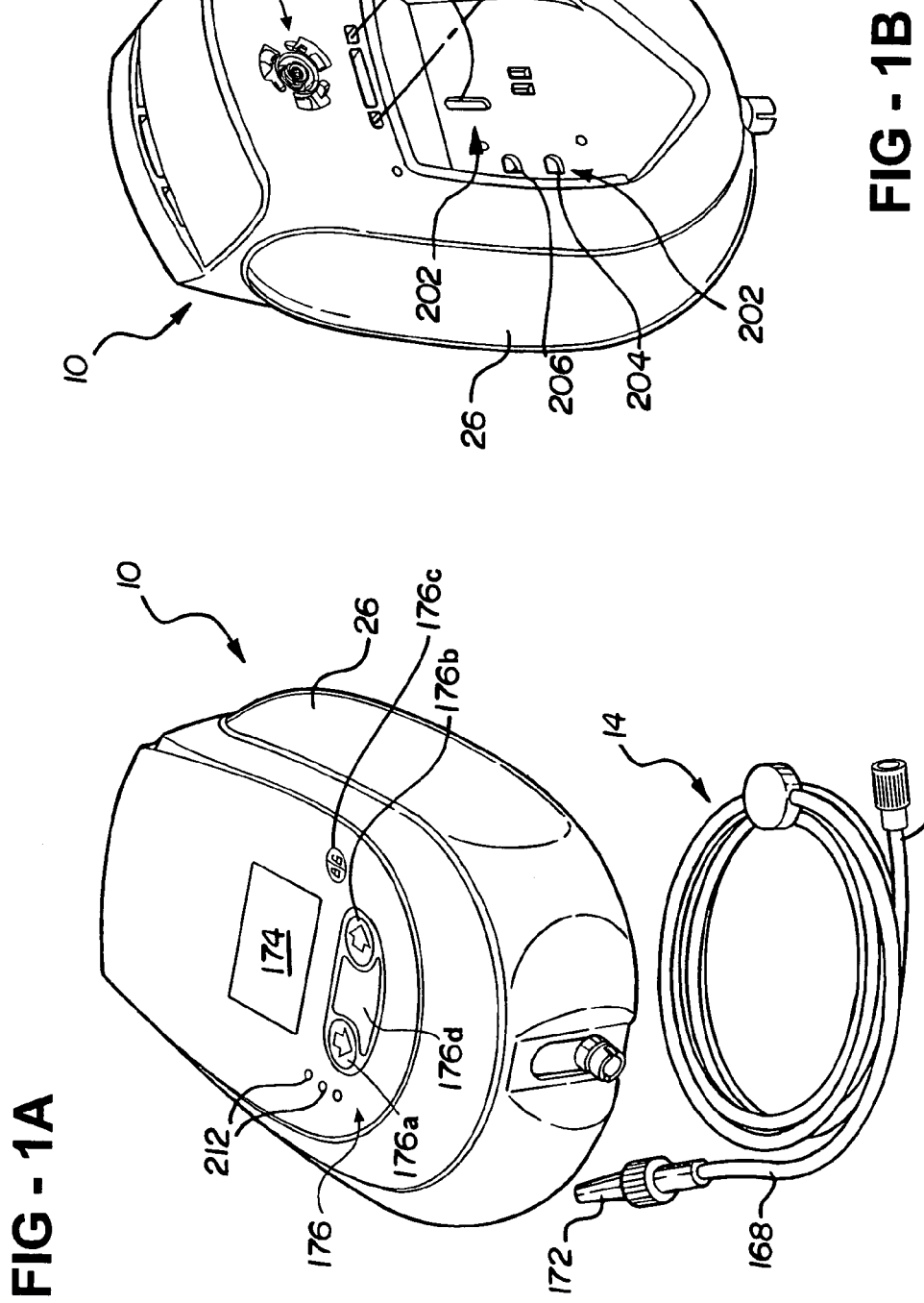
FIG. 1A is a perspective view of a fluid delivery system according to the present invention with an infusion tube set.
FIG. 1B is a perspective view of an underside of the system illustrating a system mounting clip for securing the system to a patient.

Also, as particularly disclosed in FIG. 1B, the system 10 may also further include a system mounting clip 230 that extends from an exterior facing 232 of the base 16. The system mounting clip 230 can be mounted to a belt 234 of the patient 12. Of course, it is to be understood that the system mounting clip 230 is not to be limited to a clip for a belt 234. Instead, the system mounting clip 230 may be mounted to a shirt, a pocket, and the like.

Figure 21:
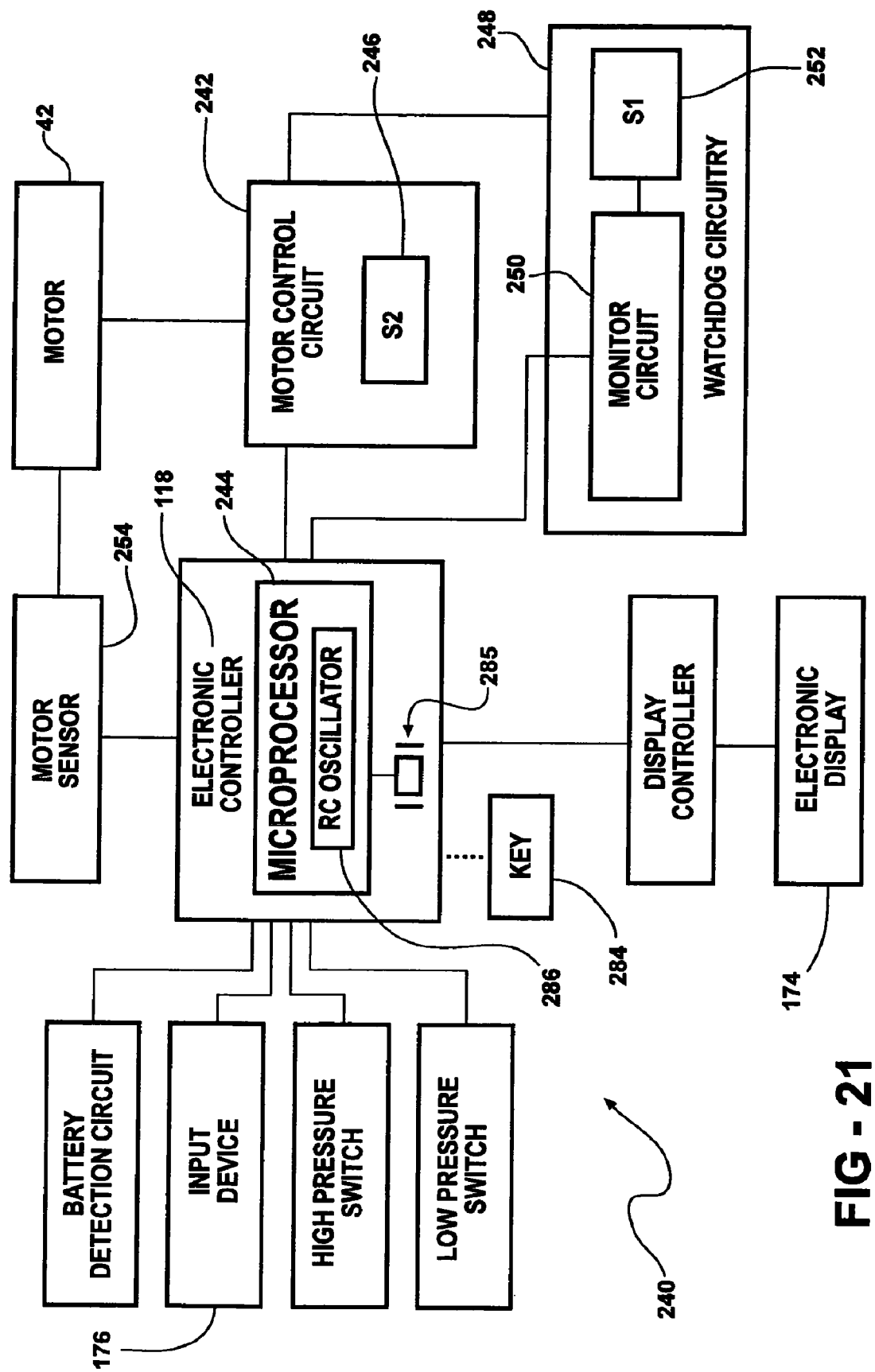
FIG. 21 is a block diagram schematically illustrating a control system.

With specific reference to FIG. 21, a control system 240 for the system 10, according to an embodiment of the present invention is shown. The control system 240 includes the electronic controller 118 and a motor control circuit 242. The electronic controller 118 controls operation of the system 10 as described above.

In one embodiment, the electronic controller 118 includes a microprocessor 244. One suitable microprocessor 244 is available from Philips Semiconductor of Sunnyvale, Calif. as model no. 87LPC764. The electronic controller 118 is programmed to control operation of the motor control circuit 242 with a computer software program. In general, the electronic controller 118 generates control signals in accordance with the computer software program and delivers the control signals to the motor control circuit 242.

The motor control circuit 242 includes a first switch 246. The first switch 246 has an open state and a closed state.

The control system 240 also includes a watchdog circuit 248 coupled to the electronic controller 118. The watchdog circuit 248 includes a monitor circuit 250 and a second switch 252. The second switch 252 has an open state and a closed state and is coupled to the first switch 246. The monitor circuit 250 is adapted to detect an abnormal condition of the control system 240 and to turn the second switch 252 off if the abnormal condition is detected. Examples of an abnormal condition include, but are not limited to, too many revolutions of the motor 42, failure of the electronic controller 118, failure of the first switch 246, or failure of a motor sensor 254 (see below).

The motor control circuit 242 is adapted to receive control signals from the electronic controller 118 and to responsively supply power to the motor 42 by placing the first switch 246 in the closed state. Power is supplied to the motor 42 if the first and second switches 246, 252 are in the closed state.

Figure 22:
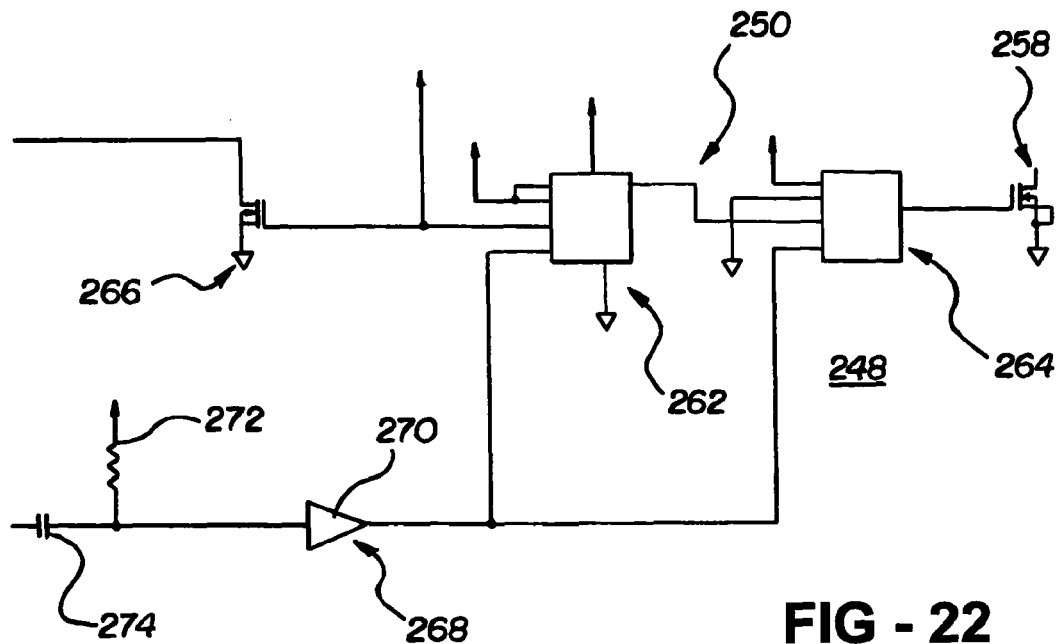
FIG. 22 is an electrical diagram illustrating portions of a watchdog circuit of the control system.
Figure 23:
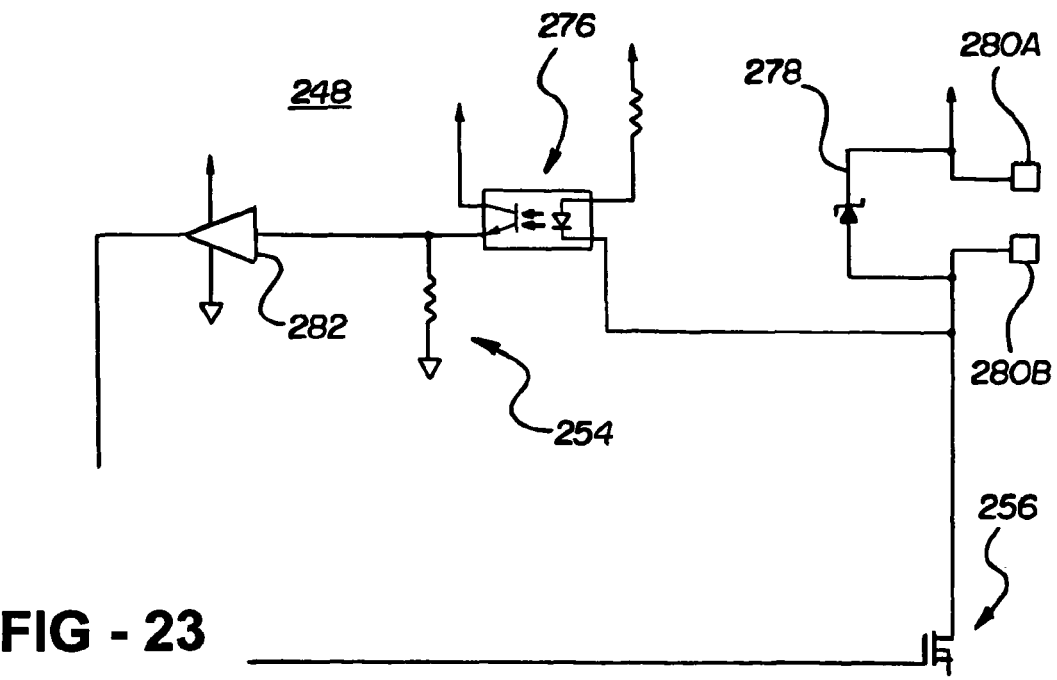
FIG. 23 is an electrical diagram illustrating further portions of the watchdog circuit of the control system.

With reference to FIGS. 22 and 23, in one embodiment the first and second switches 246, 252 are field effect transistors (FETs) 256, 258.

In one embodiment, the control system 240 includes the input device 176. A user such as a medical professional or the patient 12 is able to program the control system 240 to deliver medication at the desired flow rate using the input device 176. Based on the desired flow rate, the electronic controller 118 controls energization of the motor 42 to deliver the medication.

In one embodiment, each revolution of the motor 42 delivers a set amount of the medication during a known period of time. In order to meet the desired flow rate, the electronic controller 118 calculates a period of time between revolutions of the motor 42.

In one embodiment, the motor control circuit 242 includes the motor sensor 254 (see FIG. 4). The motor sensor 254 is coupled to the motor 42 and is adapted to detect a revolution of the motor 42 and to responsively generate a motor revolution signal in response to completion of the motor 42 revolution. In one embodiment, the motor sensor 254 is a opto-coupler sensor which is adapted to detect the presence of an indicating flag 260 (see FIG. 5) connected to the motor 42. The indicating flag 260 extends from one of the first and second outside cams 64, 66 to assist in monitoring the amount of the medication that has been delivered to the patient 12. The sensor 254 is optically-coupled with the indicating flag 260 to count revolutions of the indicating flag 260. One suitable sensor 254 is available from Omron of Schaumburg, Ill., as model no. EE-SX1109.

In one embodiment, the electronic controller 118 is adapted to reset the watchdog circuit 248 prior to sending control signals to the motor control circuit 242 to energize the motor 42. The watchdog circuit 248 is adapted to place the second switch 252 in the opened state if two motor revolution signals are received without the watchdog circuit 248 being reset.

In other words, the electronic controller 118 must reset the watchdog circuit 248 prior to or between each revolution of the motor 42. Thus, if a failure of the electronic controller 118 or the microprocessor 244 erroneously causes a control signal to be delivered to the motor control circuit 242 to continuously place the first switch 246 in the closed state, and thus, to erroneously energize the motor 42, the second switch 252 will be placed in the opened state. With the second switch 252 in the opened state, power will not be delivered to the motor 42.

Additionally, if a failure of the first switch 246 leaves the first switch 246 in the closed state, successive motor revolution signals will be received by the watchdog circuit 248 without the watchdog circuit 248 being reset and the watchdog circuit 248 will place the second switch 252 in the opened state, thus preventing power from being supplied to the motor 42.

In one embodiment, the electronic controller 118 is adapted to track the time after a motor control signal has been sent and to enter a disabled state if the time between the sent control signal and received motor revolution signal exceeds a predetermined threshold.

With specific reference to FIG. 22, in one embodiment the monitor circuit 248 includes first and second flip-flops 262, 264. The first flip-flop 262 is coupled to the electronic controller 118 and the second flip-flop 264. The second flip-flop 264 is coupled to the second FET 258.

In the illustrated embodiment, the first and second flip-flops 262, 264 are JK flip-flops. The inverse output ($\overline{Q}$) of the second flip-flop 264 is connected to the gate of the second FET 258. The clock input (CLK) of the second flip-flop 264 is coupled to the output (Q) of the first flip-flop 262. Power is supplied by the microprocessor 244 to the first and second flip-flops 262, 264 to the J and K inputs of the first flop 262 and to the J input of the second flip-flop 264. The drain of the second FET 258 is coupled to the first FET 256 and the source of the second FET 258 is connected to electrical ground.

The watchdog circuit 248 is reset by shutting off and restoring power to the first and second flip-flops 262, 264, to the J and K inputs of the first flop 262, and to the J input of the second flip-flop 264. In one embodiment, the electronic controller 118 shuts off power to the first and second flip-flops 262, 264 after each revolution of the motor 42 and supplies power prior to turning on the first switch 246 to begin the next cycle. This has two effects: conserving power and resetting the first and second flip-flops 262, 264.

The clock input (CLK) of the first flip-flop 262 is connected to the output of the motor sensor 254. The clock input (CLK) of the first flip-flop 262 is also connected to the microprocessor 244 via a third FET 266. The third FET 266 provides isolation between the microprocessor 244 and the motor sensor 254 and the monitor circuit 248. This isolation prevents a shorted pin on the electronic controller 118 from preventing revolution pulses from reaching the flip-flops 262, 264.

The inverse clear input ($\overline{CLR}$) of the first and second flip-flops 262, 264 are coupled to the microprocessor 244 via a buffer circuit 268. In the illustrated embodiment, the buffer circuit 268 includes a first buffer 270, a first resistor 272 and a capacitor 274. The electronic controller 118 may continuous supply power to the motor 42 by turning on the first switch 246 and continuously resetting the first and second flip-flops 262, 264 through the inverse clear inputs without turning off power to the flip-flops 262, 264.

In one embodiment, the flip-flops 262, 264 are triggered by logic level high ("HIGH") to logic level low ("LOW") transitions. The buffer circuit 268 prevents erroneous signal transitions when the input to the buffer circuit 268 is held HIGH by the microprocessor 244.

With specific reference to FIG. 23, the motor control circuit 242 includes the first FET 256 and the opto-coupler sensor 276. A flashback diode 278 is coupled across first and second motor junctions 280A, 280B. The opto-coupler sensor 276 is coupled to the second motor junction 280B. The transmitting diode of the opto coupler sensor 276 is coupled to power (V+) and ground through switch 256. In this arrangement the sensor 276 is only powered during the time the motor 42 is running thus conserving battery life. An output of the opto-coupler sensor 276 is coupled to the third transistor 266 via a second buffer 282.

The gate of the first FET 256 is coupled to the microprocessor 244. The drain of the first FET 256 is coupled to the motor 42 and the source of the first FET 256 is connected to the drain of the second FET 258.

As described above, the electronic controller 118 is adapted to supply medication by energizing the motor 42. A desired flow rate is achieved by energizing the motor 42 and waiting between revolutions of the motor 42 for a calculated period of time. The motor 42 is energized by turning on the first FET 256. In the illustrated embodiment, the first FET 256 is turned on by the microprocessor 244 by changing the state of the gate of the first FET 256 from LOW to HIGH. If the second FET 258 is also on, then power flows through the motor 42 and the first and second FETs 256, 258. When the motor 42 has made one (1) complete revolution, then the output of the motor sensor 254 transitions from HIGH to LOW. In the illustrated embodiment, this transition is the motor revolution signal. The motor revolution signal is also transmitted to the microprocessor 244 via the third FET 266. After receiving the motor revolution signal the microprocessor 244 turns off the first FET 256 by changing the state of the gate of the first FET 256 from HIGH to LOW.

During normal operation, the microprocessor 244 then turns off power to the first and second flip-flops 262, 264. As described above, based on the desired flow rate and the known quantity of medication delivered per revolution of the motor 42, the microprocessor 244 calculates a wait period between motor revolutions. After the wait period (or right before the wait period ends), the microprocessor 244 restores power to the first and second flip-flops 262, 264. As discussed above, this resets the first and second flip-flops 262, 264. Then the microprocessor 244 may again turn on the first FET 256 to energize the motor 42.

If a failure condition of the control system 240 exists, such as a microprocessor 244 failure or other failure, and the watchdog circuit 248 is not reset, then watchdog circuit 248 turns off the second FET 258, thereby preventing power from being supplied to the motor 42.

For example, if the microprocessor 244 fails while the first FET 256 is on, then the motor 42 will continue to be energized. The motor sensor 254 will generate motor revolution signals each time a motor revolution is completed. However, the microprocessor 244 does not or is unable to reset the watchdog circuit 248. Two successive motor revolution signals received on the CLK input of the first flip-flop 262 without the watchdog circuit 248 being reset will flip the inverse output of the second flip-flop 264 (from HIGH to LOW) and thus turn off the second FET 258.

Likewise, a failure of the first transistor 256 in the closed state will continuously energize the motor 42. If the microprocessor 244 does not reset the watchdog circuit 248, then successive motor revolution signals received on the CLK input of the first flip-flop 262 will flip the inverse output of the second flip-flop 264 and thus turn off the second FET 258.

With the second FET 258 in the off state, power will not be delivered to the motor 42.

Returning to FIG. 21, the control system 240 further includes a key 284 which is connected to the electronic controller 118 only during initialization. In one embodiment, the key 284 is part of the testing instrument 200, which is also used to test the control system 240 after it has been assembled and the batteries 45 are installed. Upon initial power-up, the control system 240 will only initialize if the key 284 is present. If the key 284 is not present, then the control system 240 enters a disabled mode and medication cannot be delivered.

In one embodiment, upon initial power-up the control system 240 sends a signal to the key 284. If present, the key 284 delivers a return signal to the control system 240 indicating its presence. The use of the key 284 ensures that the system 10 cannot be improperly reset by removing and then re-inserting the batteries 45 or other power supply 43. If this occurs and the key 284 is not present, the system 10 will not work.

The control system 240 includes a crystal 285 coupled to the microprocessor 244. The crystal 285 controls the frequency at which the microprocessor 244 operates in a conventional manner. However, if the crystal 285 is operating improperly, the microprocessor 244 could begin to operate at either a higher frequency or a lower frequency than intended. The microprocessor 244 also includes an internal oscillator 286. In one embodiment, the control system 240 is adapted to compare a frequency of the crystal 285 with a frequency associated with the internal oscillator 286. The electronic controller 118 adapted to compare a difference between the first and second frequencies and enter a disabled state if the difference is greater than a predetermined threshold. Thus, if the crystal 285 experiences a failure, the control system 10 will be disabled.

Figure 24:
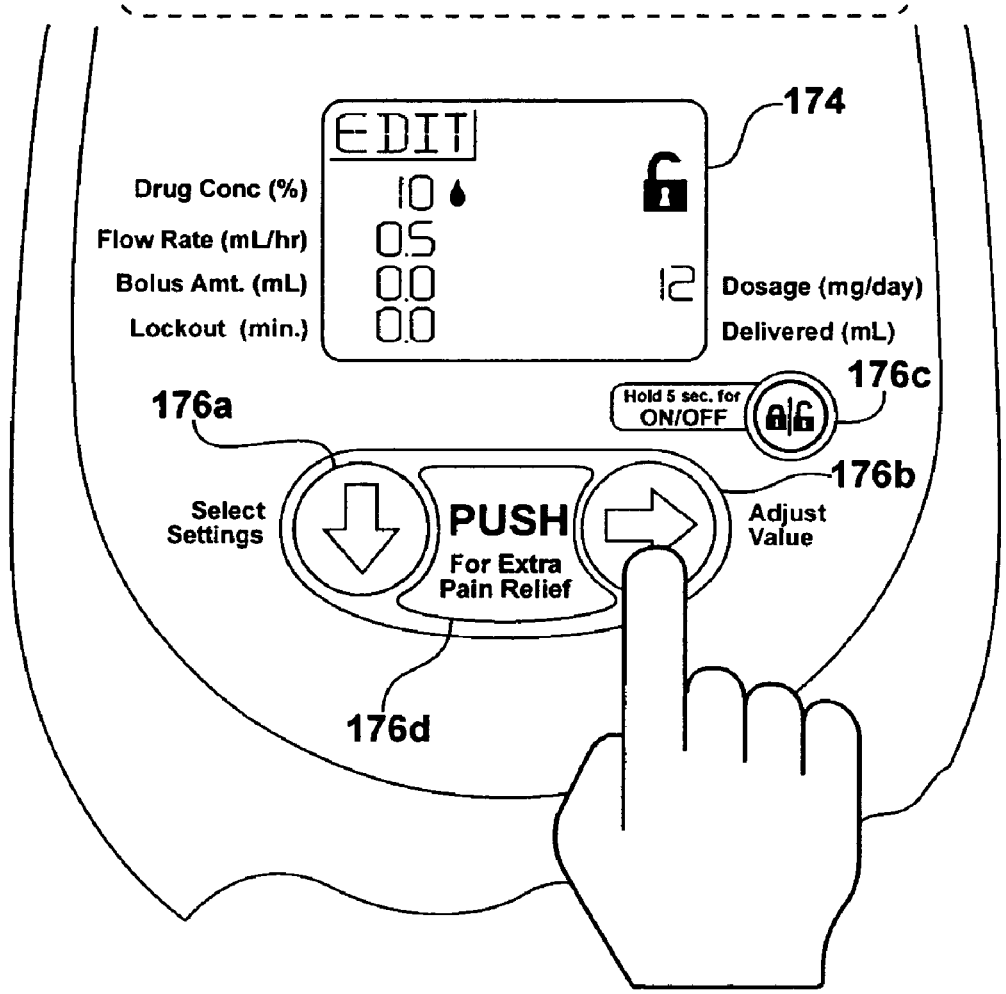
FIG. 24 illustrates a top view of the system with set-up instructions on an overlay label for programming the system.

Referring to FIGS. 2B, 24, 25A-25F, 26, and 27A-27B, the present invention further provides a method of controlling the system 10. This method is designed to be convenient for users, e.g., medical professionals and/or the patient 12. Referring to FIG. 24, a removable overlay label 238, having a set of explanatory indicia, i.e., instructions, is mounted, preferably adhered, to the system 10. According to the overlay label 238, the method of setting the system 10 includes first activating the system 10 using the input device 176, e.g., by depressing any of the touch sensitive elements 176a-d (hereinafter "buttons" 176a-d), to activate the system 10. The buttons 176a-d may be touch-sensitive areas on a touch screen display or raised buttons for depressing. In other embodiments, the input device 176 may be voice-activated. Next, using the "select settings" button 176a, the user can scroll through the operating parameters to be set and use the "adjust value" button 176b to adjust values of the operating parameters accordingly. This is illustrated in FIGS. 25A-25D where the value adjacent to indicia indicating the operating parameter to be set blinks as the user scrolls through the operating parameters.

The operating parameters to be set include drug concentration, flow rate, bolus amount, and bolus lockout time. These parameters are well known to those skilled in the art and will not be described in detail, except to say that the bolus lockout time, once set, and once the system 10 is operating, includes a countdown timer that begins to countdown from the established lockout time until zero, with the time remaining displayed on the display 174. When the display indicates zero time remaining, another bolus can be delivered to the patient. Other parameters, not mentioned, could also be set.

Figures 25A, 25B, 25C, 25D, 25E, 25F:
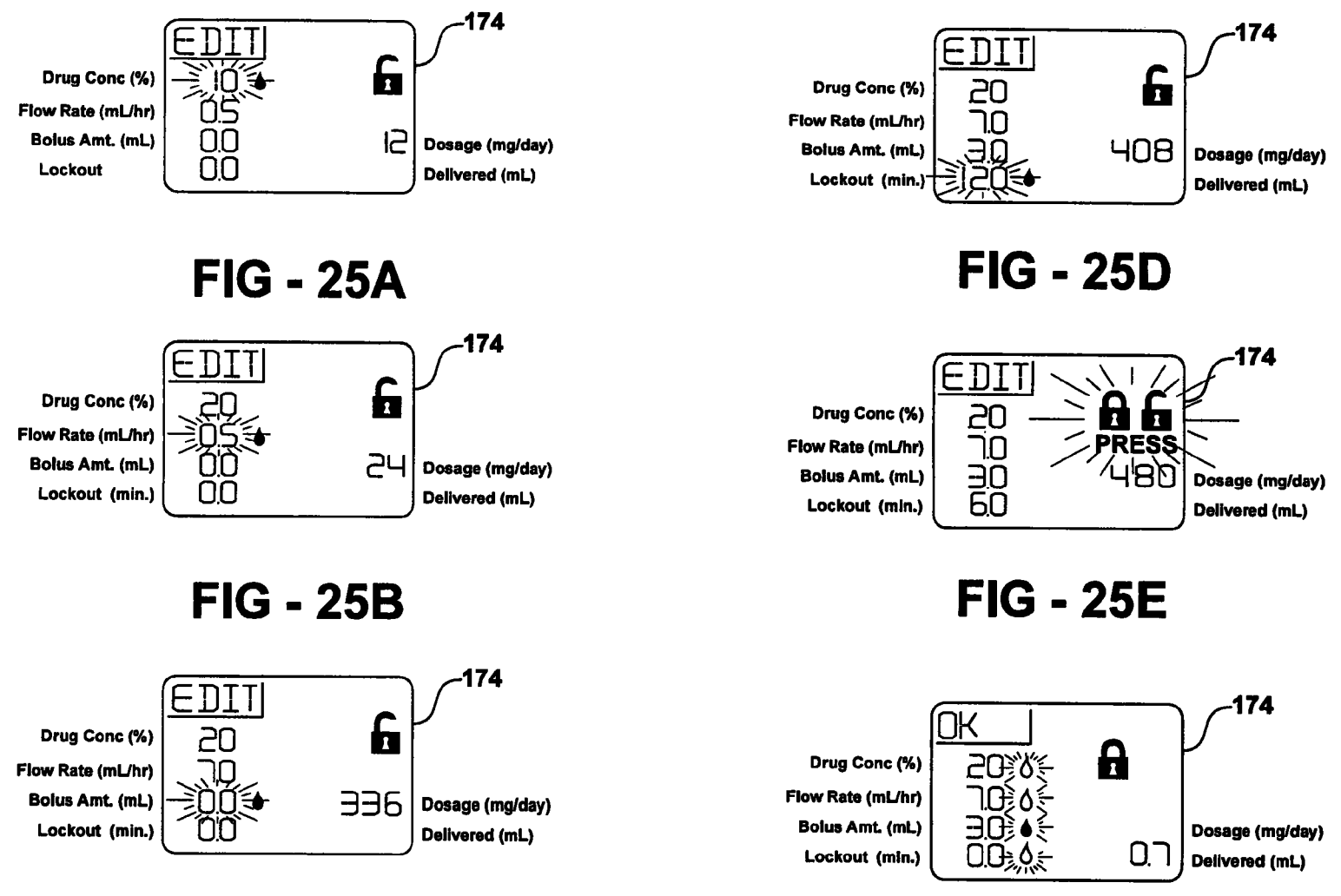

Referring to FIG. 25E, after the operating parameters have been set, i.e., values for the operating parameters have been established, the system 10 can be locked such that the operating parameters are unable to be modified. After the user is satisfied with his or her selections, the user depresses a "lock/unlock" button 176c, reviews his or her selections, and then depresses the lock/unlock button 176c again to lock the settings and activate the system 10. Once the system 10 is locked, the user can remove the removable overlay label 238. To accomplish this, the user, either the medical professional or the patient 12, simply pulls the removable overlay label 238 off the system 10. The lock/unlock button 176c is also configured to turn the system 10 on and off, by depressing the lock/unlock button 176c for a predetermined period of time, such as five seconds. Once the system 10 is locked, the system 10 is designed to be convenient for use by the patient 12.

The system 10, when locked, is configured to prevent the patient 12 or other persons from altering any of the operating parameters during use. As a result, the select settings 176a and adjust value 176b buttons cease to function in the same manner as when the system 10 was unlocked. In other words, when the lock/unlock button 176c is depressed to lock the settings, a signal is transmitted to the controller 118 and the controller 118 alters the functionality of the buttons 176a-d, as is appreciated by those skilled in the art, to prevent the user from resetting the operating parameters. However, in some instances, it is desirable to allow the user, particularly the medical professional, to reset the operating parameters, such as when increased delivery rates of medication are needed by the patient 12. To facilitate this need, the system 10 is also capable of being unlocked to allow the user to reset the operating parameters in the manner previously described. The system 10 uses a code 236 or password, entered using the input device 176, and transmitted to and received by the controller 118, to unlock the system 10.

Referring to FIG. 26, the code 236 is at least periodically displayed on the display 174 during use. In this embodiment, periodic can be defined as being at predefined time intervals or at random times. In a preferred embodiment, the code 236 is continuously displayed on the display 174 during use. In one embodiment, the code 236 comprises alphanumeric characters or values based on or associated with the set values of the operating parameters, or at least portions thereof. For instance, the set values for the operating parameters in FIG. 26 include a drug concentration of 1.00, a flow rate of 12.0 mL per hour, a bolus amount of 3.0 mL, and at this point in time, the countdown timer of the bolus lockout time is at 102 minutes. The code 236 comprises the set values of the operating parameters corresponding to a predetermined pattern of values as displayed on the display 174. In FIG. 26, the predetermined pattern is shown by dashed lines. In this case, the predetermined pattern provides a code 236 of "0201".

Since the countdown timer of the bolus lockout time comprises a portion of the code 236, and the countdown timer displayed on the display 174 changes with time, then the code 236 also changes with time, or is altered based on a predetermined time interval. Here, since the first column of the countdown timer is used to determine the code 236, the code changes every one hundred minutes while the bolus lockout time is counting down. Other predetermined time intervals could also be used. Preferably, the code 236 is altered at least once during use of the system 10.

Furthermore, the code 236 could also be another combination or predetermined pattern of the values displayed on the display 174. For instance, still referring to FIG. 26, the code 236 could be the first column of the set value for concentration, the second column of the set value for flow rate, the second column of the set value for bolus amount, and the third column of the countdown timer. In this instance, the code 236 would be "1232" and would change every minute. In other words, alternative predetermined patterns of the alphanumeric characters displayed on the display 174, either continuously, or at least periodically, could be used to define the code 236.

Referring to FIGS. 27A and 27B, once the code 236 is obtained, the user presses the lock/unlock button 176c for a predetermined time period, preferably less than a second, and the set values of the operating parameters disappear from the display 174. The user then enters the code 236 into their respective positions on the display 174 using the select settings 176a and adjust value 176b buttons. Once the code 236 is entered, the lock/unlock button 176c is depressed. If the code 236 was entered properly, the system 10 unlocks to allow the user to reset the operating parameters as discussed above, including re-locking the system 10 after the values of the operating parameters are reset. In other words, when the code 236 is properly entered, the controller 118 is programmed to reset the functionality of the buttons 176a-d to allow the user to reset the operating parameters. If the code 236 is not properly entered, the user is given a predetermined number of unsuccessful entry attempts in a predetermined time period, such as five attempts in thirty minutes. If the number of unsuccessful attempts exceeds the predetermined number, the input device 176 will be locked for a predetermined time period before allowing further attempts to enter the code 236. In other words, the user will be restricted from entering the code 236 for the predetermined time period.

In operating the system 10, the system 10 may be deactivated, if necessary, to stop delivery of the medication to the patient 12. To deactivate the system 10, the patient 12 depresses the lock/unlock button 176c as described above. If the system 10 is deactivated, then the patient 12 may also use the lock/unlock button 176c to activate the system 10 to re-start delivery of the medication to the patient 12.

In operating the system 10, the patient 12 may request an additional amount of the medication relative to the selected amount of the medication, and provided the bolus amount will not be violated, the patient 12 will receive an additional amount of the medication. To request an additional amount of the medication relative to the selected amount, the patient 12 actuates a bolus button 176d. Those skilled in the art appreciate that the controller 118 is programmed in a known manner to carry out these and other functions of the system 10.

Figure 28:
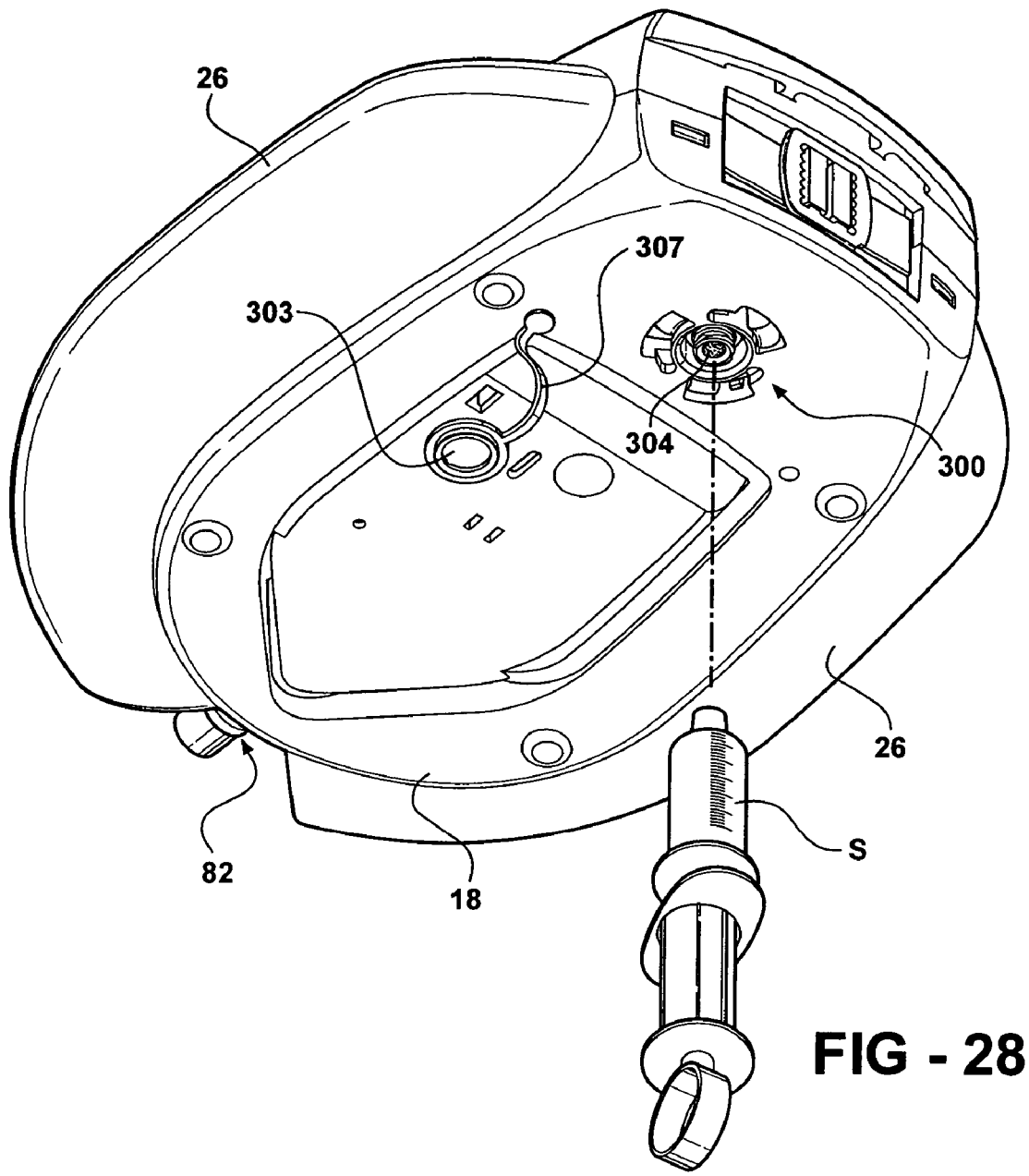
FIG. 28 is a perspective view of a bottom side of the system indicating a position of a refill port of the system.
Figure 30:
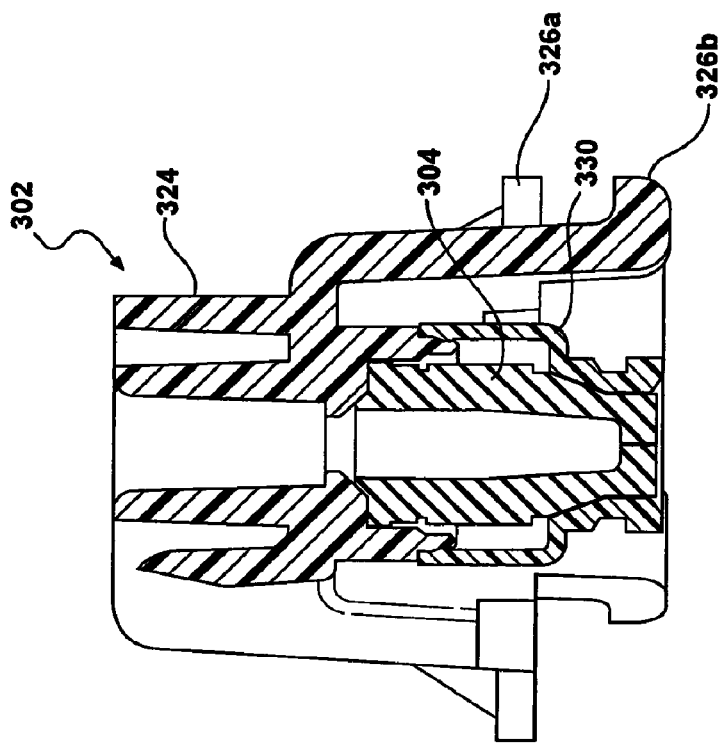
FIG. 30 is a cross-sectional view of the valve.
Figure 29:
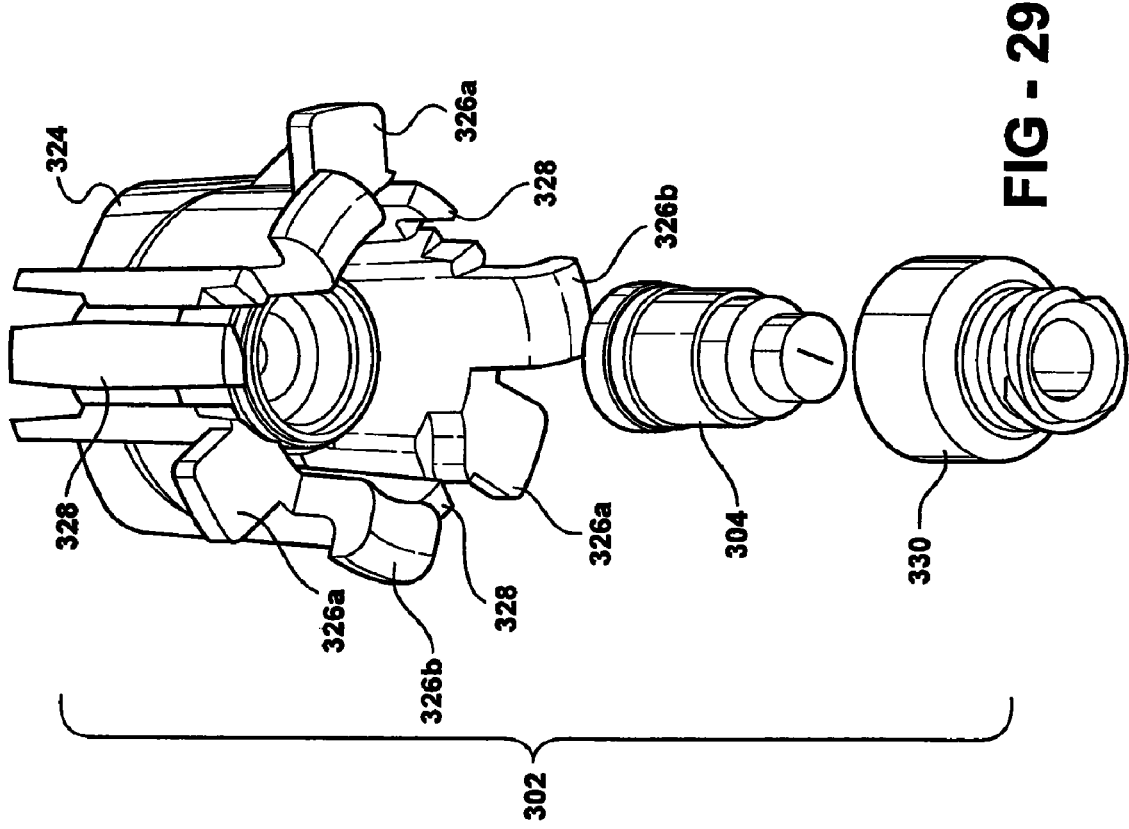
FIG. 29 is an exploded view of a valve used as the refill port of the system.

Referring to FIGS. 28-39, the refill port 300 is shown. By using the refill port 300, the fluid, e.g., medication, can be added to the reservoir 24 such that the system 10 is more suitable for procedures in which large quantities of medication are required, without disconnecting the infusion tube set 14 from the port 82. Referring specifically to FIGS. 29 and 30, the refill port 300 includes a slit-type swabable valve 302 such as the valve shown in U.S. Pat. No. 6,651,956, hereby incorporated by reference, and commercially available from Halkey-Roberts Corporation of St. Petersburg, Fla. The valve 302 is mounted to the base 18 such that a valve stem 304 with slit (or other penetrable septum member) is accessible from a bottom of the system 10, as shown in FIG. 28. A removable port cap 303 is attached to the base 18 by a leash 307 for covering the valve stem 304 when not in use.

With reference to FIG. 29, the valve 302 includes three basic components, a luer body 330, the valve stem 304, and a valve body 324. The luer body 330 and the valve stem 304 are further discussed in the '956 patent incorporated herein. The valve body 324 of the valve 302 includes upper 326a and lower 326b tabs and snap-lock fingers 328 to secure the valve body 324 to the base 18 of the system 10. FIG. 30 illustrates the valve body 324 mounted to the luer body 300 such as by ultrasonic welding, adhesive, or the like. The valve stem 304 is captured between the valve body 324 and the luer body 300.

Figure 31:
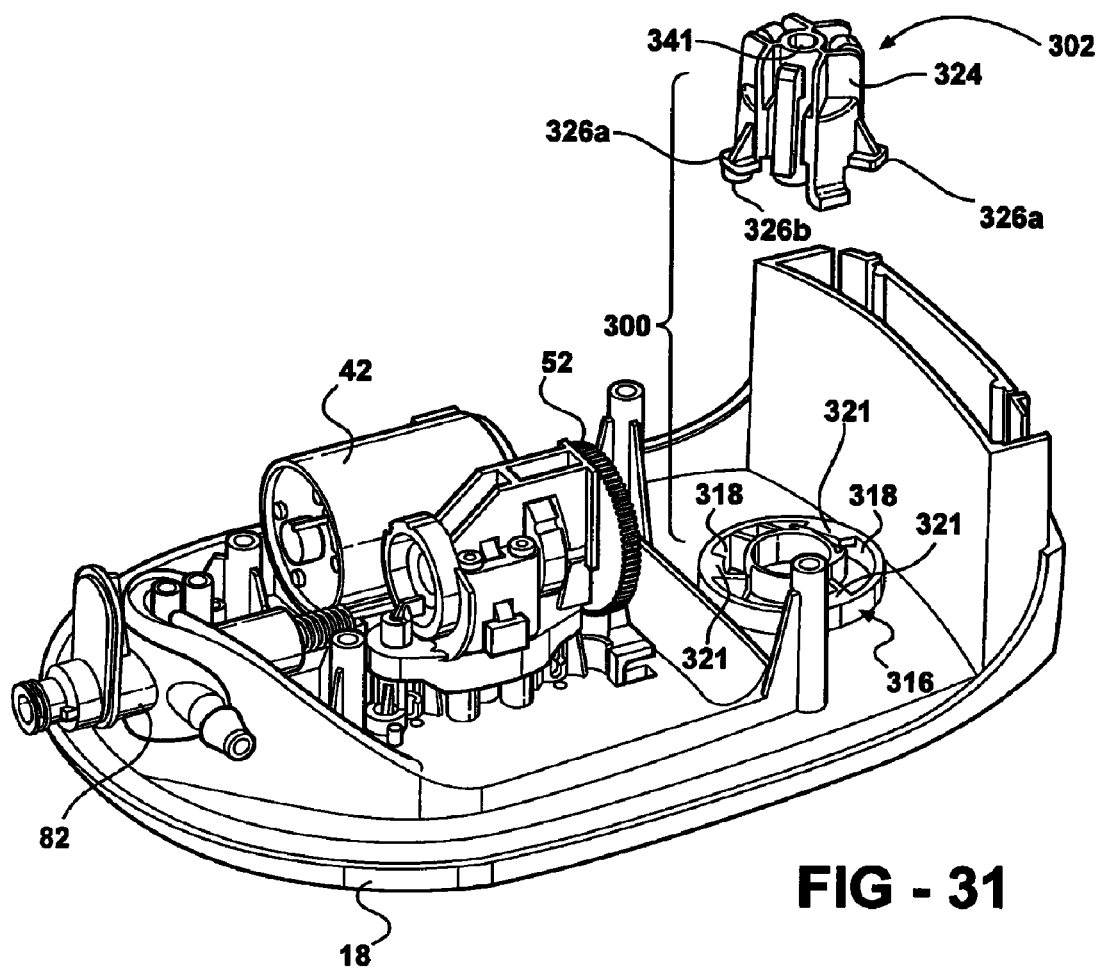
FIG. 31 is a perspective assembly view of the valve and the base.
Figure 32:
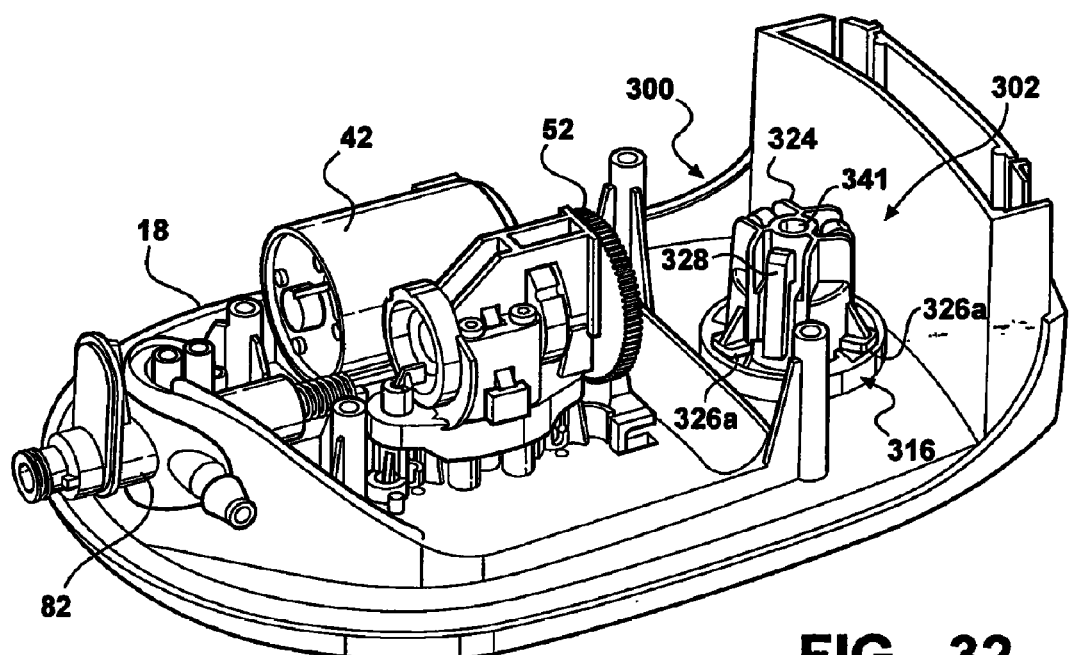
FIG. 32 is a perspective view of the valve and the base.
Figure 33:
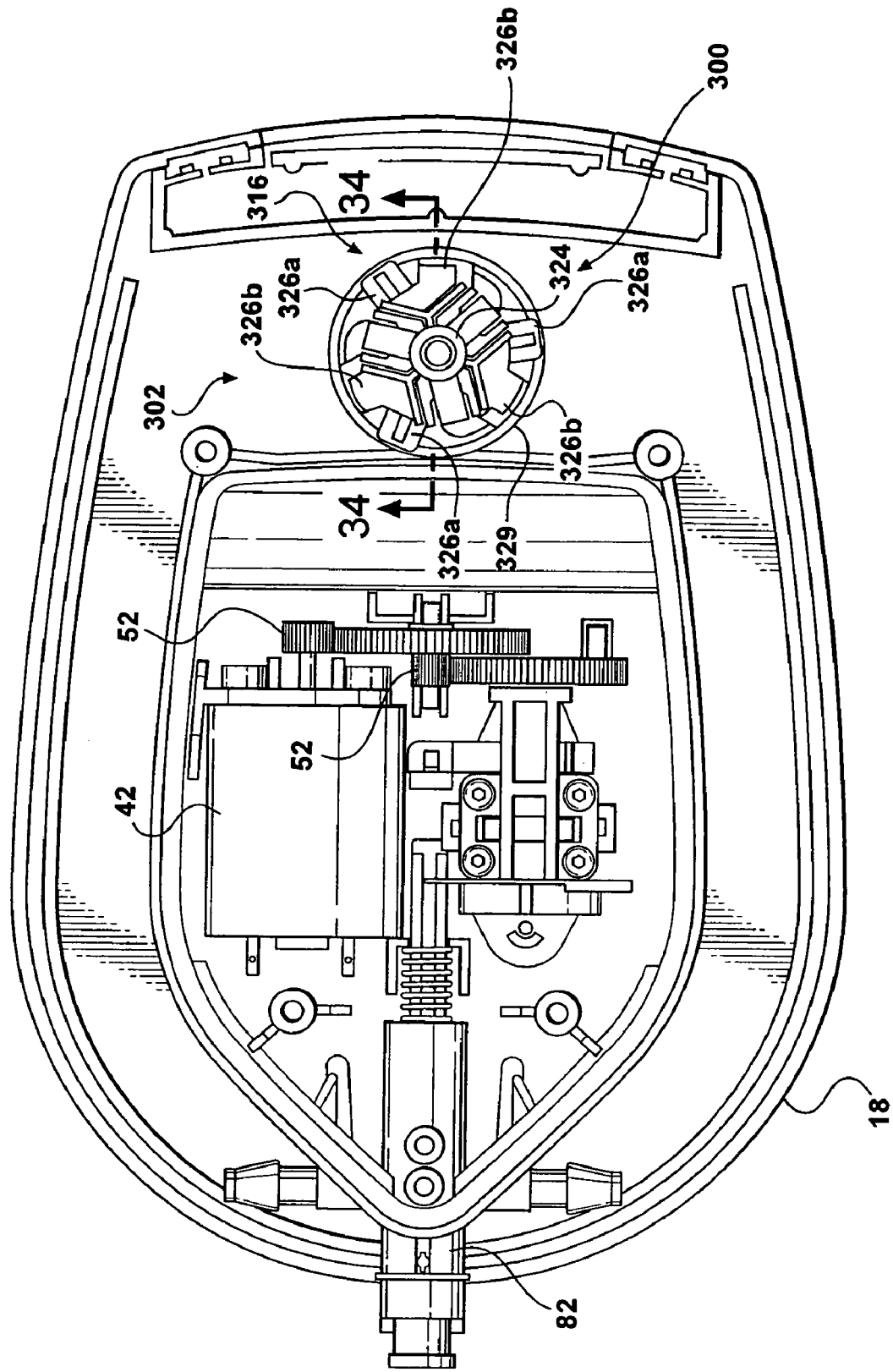
FIGS. 33-35 are various views of the valve inserted in the base in an unlocked position.
Figure 34:
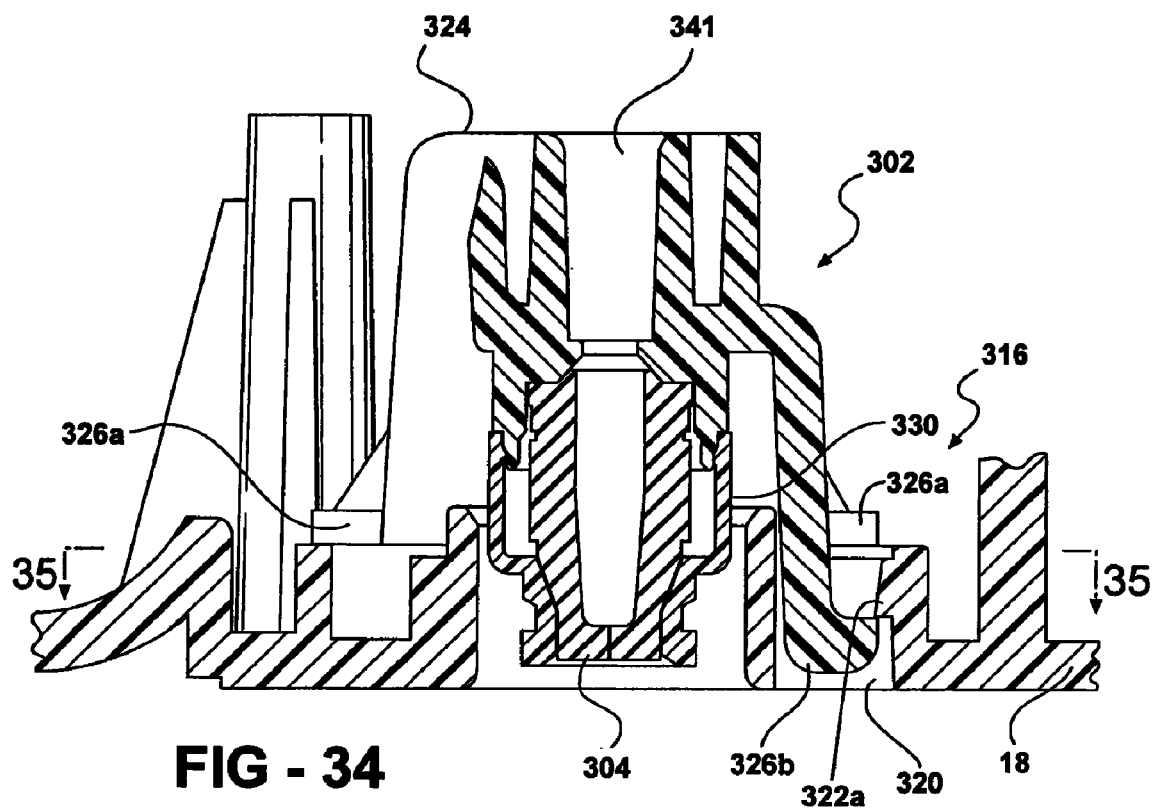
Figure 35:
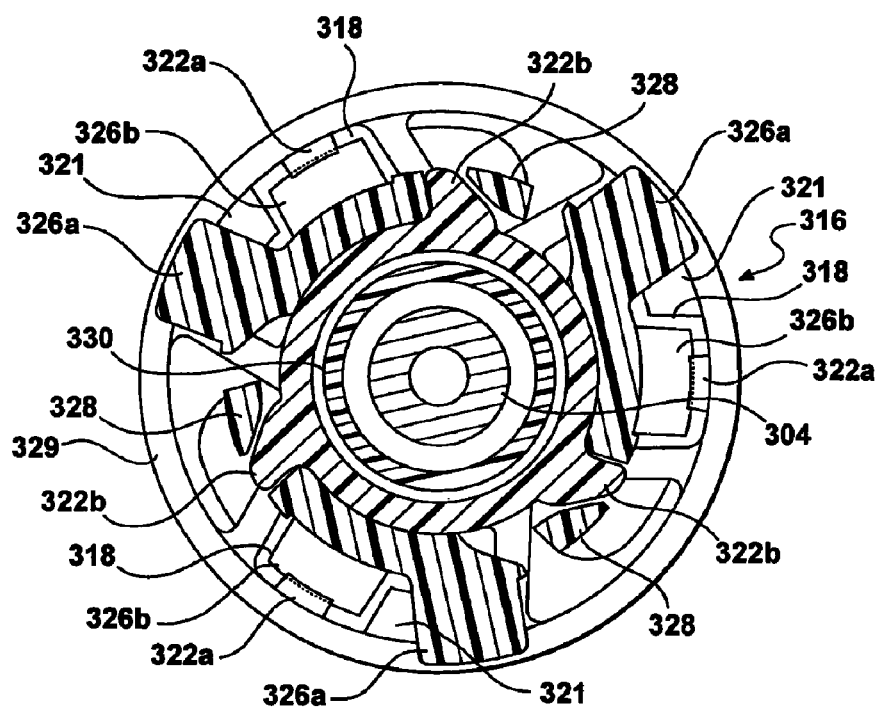

With reference to FIGS. 31 and 32, a valve mount 316 is integrally formed in the base 18 to mount the valve body 324 to the base 18. The valve mount 316 is designed with a low profile. Referring to FIGS. 33-35, the valve mount 316 includes notches 318 and a groove 320 for receiving the lower tabs 326b of the valve body 324. The valve mount 316 also includes cammed portions 322a, 322b to rotatably and axially lock the valve body 324 to the valve mount 316. More specifically, the upper 326a and lower 326b tabs and snap-lock fingers 328 of the valve body 324 co-act with the notches 318, groove 320, tab guides 321, and cammed portions 322a, 322b of the valve mount 316 to secure the valve body 324 to the valve mount 316 in a snap-locked manner to rotationally and axially restrain the valve body 324 to the base 18.

In FIGS. 33-35, the valve body 324 is inserted into the valve mount 316, but not yet locked in position. The lower tabs 326b of the valve body 324 are lowered through the notches 318 and springably slide over the cammed portions 322a in the valve mount 316 such that the lower tabs 326b rest in the groove 320. The upper tabs 326a rest above an upper surface of an outside wall 329 of the valve mount 316.

Figure 36:
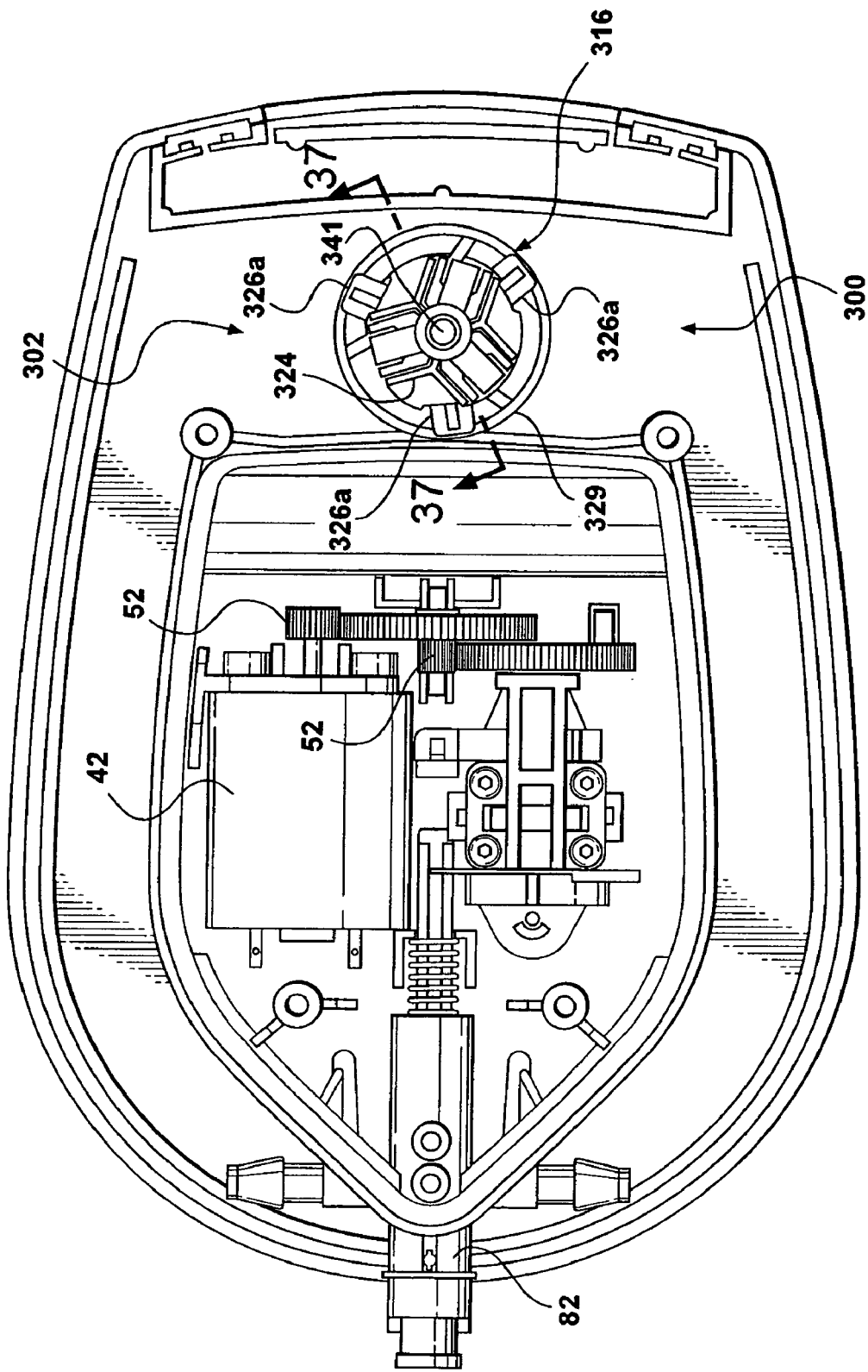
FIGS. 36-38 are various views of the valve inserted in the base in a locked position.
Figure 37:
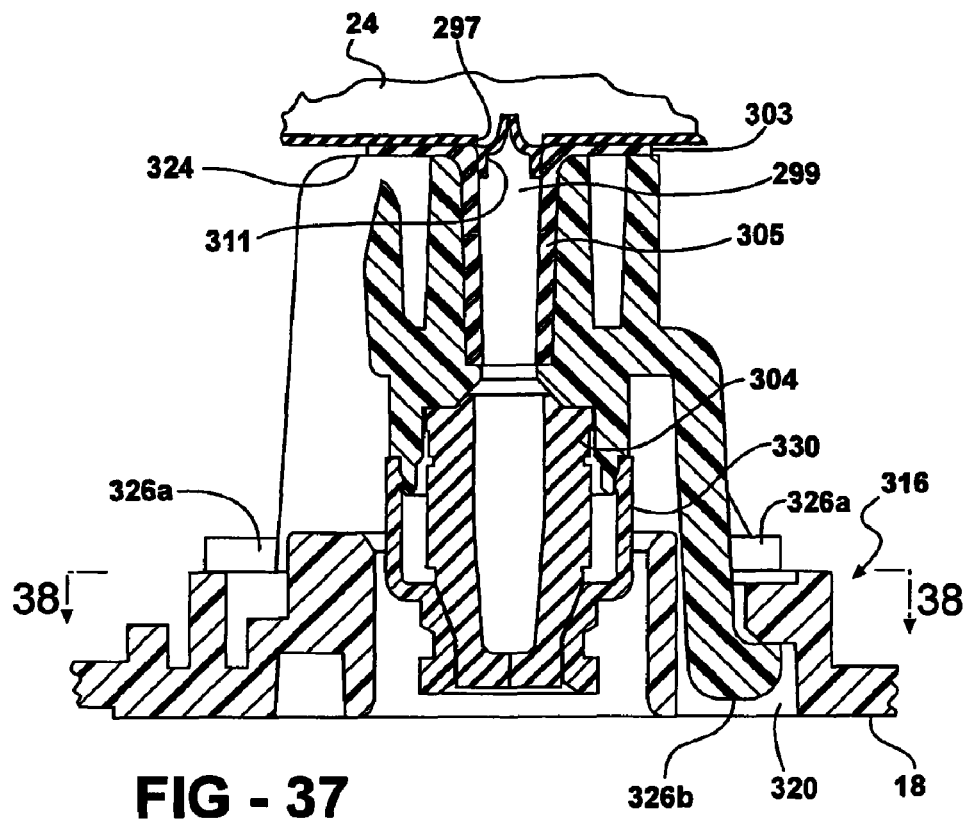
Figure 38:
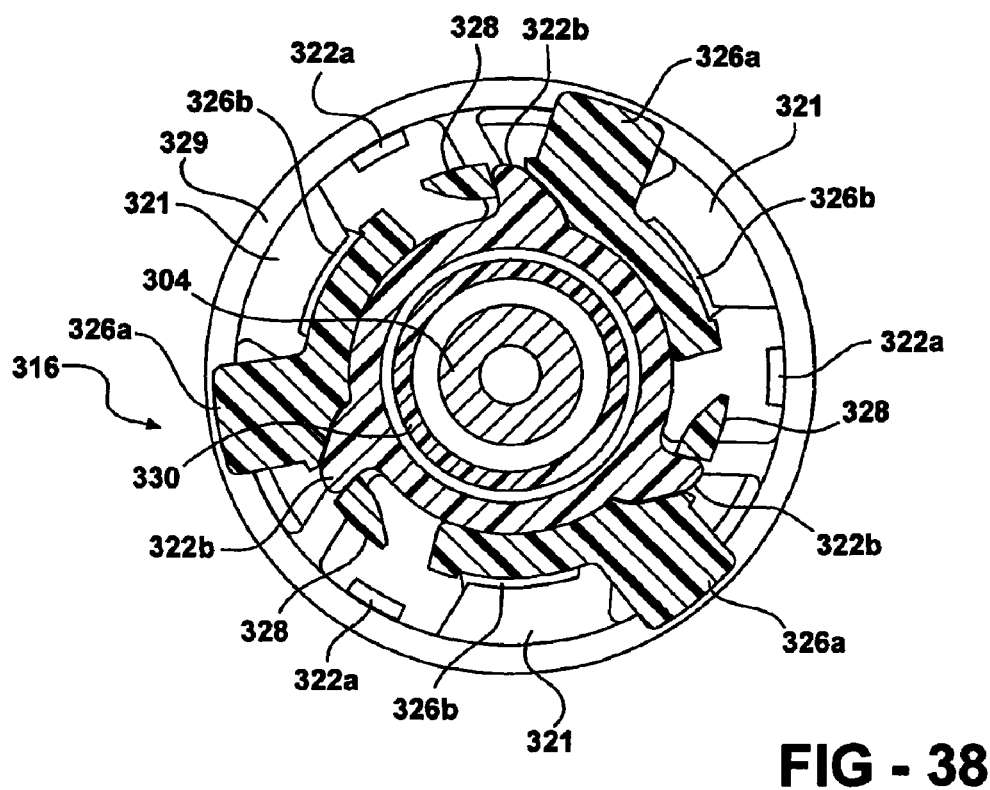

In FIGS. 36-38, the valve body 324 is shown rotated counter-clockwise relative to the valve mount 316 to snap-lock the valve body 324 to the valve mount 316. Here, the snap-lock fingers 328 (which include cammed edges) ride over the cammed portions 322b of the valve mount 316 and snap-lock into position to prevent any clockwise rotation. The shape of the snap lock fingers 328 is optimized to stay below stress yield points during insertion into their snap-locked positions, while retaining sufficient rigidity to prevent disassembly during syringe removal. At the same time, the lower tabs 326b abut stops (not shown) in the valve mount 316 to prevent any further counter-clockwise rotation. As a result, the valve body 324 is rotatably locked relative to the valve mount 316. Simultaneously, the lower tabs 326b ride below the tab guides 321 of the valve mount 316 to prevent any further axial movement of the valve body 324 relative to the valve mount 316 in one direction, while the upper tabs 326a rest above the outside wall 329 of the valve mount 316 to prevent axial movement in the opposite direction.

Referring to FIG. 39, a flanged connector 301 is used to provide fluid communication between the valve 302 and the reservoir 24. As shown, an opening 297 is formed in one side of the reservoir 24 (shown here in a deflated state). The flanged connector 301, which includes a flange 303 and a stem 305 having an opening 299 defined therethrough, is secured to the reservoir 24 at the opening 297. More specifically, the flange 303 is ultrasonically welded, or adhered using an adhesive or other methods, to the reservoir while the openings 297, 299 are aligned to provide fluid communication with an interior of the reservoir 24. Once the flanged connector 301 is fixed to the reservoir 24, the stem 305 is inserted into an orifice 341 defined through the valve body 324 and secured thereto by ultrasonic welding, adhesive, or the like. This step usually occurs after the valve body 324 is snap-locked to the valve mount 316. As a result, the reservoir 24 is placed in fluid communication with the valve stem 304 such that when a fluid filling device, such as a syringe S, is attached to the luer body 330, the syringe penetrates the slit in the valve stem 304 and fluid communication is provided between the syringe S and the reservoir 24 to refill the reservoir 24 of the system 10.

In addition to any fluid holding capability of the valve stem 304, a one-way valve, such as a duck-billed valve 311 shown in FIG. 37, may be mounted (ultrasonically welded, adhered, etc.) inside the stem 305 or at some other convenient location to prevent the fluid from leaking out of the refill port 300.

During use, the port cap 303 is first removed from the refill port 300. Then, the valve stem 304 is swabbed for sterility per standard protocol. The syringe S is then filled with the fluid, e.g., medication, and once excess air is removed from the syringe S, the syringe S is luer-locked to luer body 330 and the fluid transferred from the syringe S into the reservoir 24. This can be repeated until the reservoir 24 is refilled. Once complete, the port cap 303 is replaced. If the system 10 is displaying the empty symbol on the display 174, the lock/unlock button 176c can be depressed to reactivate the system 10.

Obviously, many modifications and variations of the present invention are possible in light of the above teachings. Also, it is to be understood that reference numerals are merely for convenience and are not to be in any way limiting.

What is claimed is:

1. A system for delivering fluid to a patient, comprising:
   a reservoir for storing the fluid to be delivered to the patient;
   a fluid discharge device operatively coupled to said reservoir for delivering the fluid from said reservoir to the patient;

a controller that operates said fluid discharge device;

an input device in electronic communication with said controller to set at least one operating parameter of said system wherein said controller operates said fluid discharge device based on said at least one operating parameter and locks said system after said at least one operating parameter is set such that said at least one operating parameter is unable to be modified; and a display in electronic communication with said controller that displays a plurality of alphanumeric characters and a code defined by a predetermined pattern of said alphanumeric characters wherein said code changes at least once during use of said system, said controller unlocking said system upon receiving said code thereby allowing a user to reset said at least one operating parameter.

2. A system as set forth in claim 1 wherein said code is associated with said at least one operating parameter.

3. A system as set forth in claim 2 wherein said at least one operating parameter includes a value and said code comprises at least a portion of said value.

4. A system as set forth in claim 1 wherein said input device is configured for setting a plurality of operating parameters, each of said plurality of operating parameters having a value and said code comprising at least a portion of each of said values.

5. A system as set forth in claim 4 wherein said plurality of operating parameters includes concentration, flow rate, bolus amount, and bolus lockout time.

6. A system as set forth in claim 5 including a countdown timer for counting down said bolus lockout time wherein said code is based on said countdown timer and is altered as said countdown timer changes time.

7. A system as set forth in claim 1 wherein said code is continuously displayed on said display.

8. A system as set forth in claim 7 wherein said code is altered at predetermined time intervals.

9. A system as set forth in claim 1 including a housing for supporting said reservoir, said fluid discharge device, said controller, and said input device.

10. A system as set forth in claim 1 wherein said input device includes at least one touch sensitive element for entering said code into said controller using said input device.

11. A system as set forth in claim 1 wherein said system is portable and configured to be carried by a patient.

12. A system as set forth in claim 1 wherein said input device is configured for setting a plurality of operating parameters, each of said plurality of operating parameters having a value and said code being displayed on said display in a predetermined pattern that includes at least a portion of each of said values.

* * * * *